(12) United States Patent
Paulicka et al.

(10) Patent No.: US 11,426,727 B2
(45) Date of Patent: Aug. 30, 2022

(54) ACOUSTOPHORETIC LYSIS DEVICES AND METHODS

(71) Applicant: Siemens Healthcare Diagnostics Inc., Tarrytown, NY (US)

(72) Inventors: Peter Paulicka, Röttenbach (DE); Jeffrey Jasperse, Newton, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/593,882

(22) PCT Filed: Apr. 26, 2021

(86) PCT No.: PCT/US2021/029119
§ 371 (c)(1),
(2) Date: Sep. 27, 2021

(87) PCT Pub. No.: WO2021/222084
PCT Pub. Date: Nov. 4, 2021

(65) Prior Publication Data
US 2022/0143611 A1 May 12, 2022

Related U.S. Application Data

(60) Provisional application No. 63/016,537, filed on Apr. 28, 2020.

(51) Int. Cl.
*B01L 3/00* (2006.01)
*B01L 9/00* (2006.01)
*C12N 1/06* (2006.01)

(52) U.S. Cl.
CPC ..... *B01L 3/502715* (2013.01); *B01L 3/50273* (2013.01); *B01L 3/502707* (2013.01);
(Continued)

(58) Field of Classification Search
None
See application file for complete search history.

(56) References Cited

U.S. PATENT DOCUMENTS 4,854,170 A 8/1989 Brimhall et al.
5,371,020 A 12/1994 Frischauf
(Continued)

FOREIGN PATENT DOCUMENTS

EP 1060025 B1 10/2003
EP 1165748 B1 6/2004
(Continued)

OTHER PUBLICATIONS

Laurell, Thomas et al., "Chip integrated strategies for acoustic separation and manipulation of cells and particles", Chemical Society Reviews, Sep. 29, 2006, 15 pages.
(Continued)

*Primary Examiner* — Jennifer Wecker
*Assistant Examiner* — Bryan Kilpatrick

(57) ABSTRACT

Lysis devices, methods, and systems are disclosed including a lysis device comprising a sample vessel having an outer surface, a microchannel within the confines of the outer surface, a first port extending through the outer surface to the microchannel, and a second port extending through the outer surface to the microchannel; and an acoustic transducer bonded to the outer surface of the sample vessel to form a monolithic structure, the acoustic transducer configured to emit ultrasonic acoustic waves into and/or to induce shear forces into a blood sample within the microchannel, thereby rupturing the blood cells.

22 Claims, 15 Drawing Sheets

(52) U.S. Cl.
CPC ............. *B01L 9/527* (2013.01); *C12N 1/066* (2013.01); *B01L 2200/027* (2013.01); *B01L 2200/028* (2013.01); *B01L 2200/04* (2013.01); *B01L 2200/12* (2013.01); *B01L 2200/14* (2013.01); *B01L 2200/16* (2013.01); *B01L 2300/0663* (2013.01); *B01L 2300/12* (2013.01); *B01L 2400/0436* (2013.01); *B01L 2400/0487* (2013.01)

(56) References Cited

U.S. PATENT DOCUMENTS

| | | |
|---|---|---|
| 5,652,141 A | 7/1997 | Henco et al. |
| 5,902,489 A | 5/1999 | Yasuda et al. |
| 6,043,080 A | 3/2000 | Lipshutz et al. |
| 6,071,239 A | 6/2000 | Cribbs et al. |
| 6,100,084 A | 8/2000 | Miles et al. |
| 6,216,538 B1 | 4/2001 | Yasuda et al. |
| 6,431,476 B1 | 8/2002 | Taylor et al. |
| 6,442,411 B1 | 8/2002 | Guthermann |
| 6,739,531 B2 | 5/2004 | Taylor |
| 6,819,027 B2 | 11/2004 | Saraf |
| 6,929,750 B2 | 8/2005 | Laurell et al. |
| 6,936,696 B2 | 9/2005 | Llorin et al. |
| 6,942,169 B2 | 9/2005 | Sparks |
| 6,980,285 B1 | 12/2005 | Hansen |
| 7,192,557 B2 | 3/2007 | Wu et al. |
| 7,338,802 B2 | 3/2008 | Frischauf et al. |
| 7,704,743 B2 | 4/2010 | Fedorov et al. |
| 7,723,095 B2 | 5/2010 | Cleuziat et al. |
| 7,959,862 B2 | 6/2011 | Cho et al. |
| 8,169,122 B1 | 5/2012 | Roberts et al. |
| 8,637,285 B2 | 1/2014 | Ussing |
| 8,641,971 B2 | 2/2014 | Van Doorn et al. |
| 8,859,272 B2 | 10/2014 | Hwang et al. |
| 8,900,859 B2 | 12/2014 | Dziewiszek et al. |
| 8,969,058 B2 | 3/2015 | Stone |
| 9,096,823 B1 | 8/2015 | Branch et al. |
| 9,097,701 B2 | 8/2015 | Krogh |
| 9,127,306 B2 | 9/2015 | Bashkirov et al. |
| 9,206,416 B2 | 12/2015 | Krishnan et al. |
| 9,217,132 B2 | 12/2015 | Eshoo et al. |
| 9,278,027 B2 | 3/2016 | Sussaman |
| 9,416,776 B2 | 8/2016 | Ledden et al. |
| 9,506,028 B2 | 11/2016 | Yang et al. |
| 9,512,421 B1 | 12/2016 | Branch et al. |
| 9,683,931 B2 | 6/2017 | Andersen et al. |
| 9,695,390 B2 | 7/2017 | Weitz et al. |
| 9,719,128 B2 | 8/2017 | Fuchs et al. |
| 9,873,119 B2 | 1/2018 | Eshoo et al. |
| 10,072,258 B2 | 9/2018 | Faltin et al. |
| 10,190,148 B2 | 1/2019 | Charles et al. |
| 10,407,711 B2 | 9/2019 | Charles et al. |
| 10,564,147 B2 | 2/2020 | Doria et al. |
| 10,585,023 B2 | 3/2020 | Broyer et al. |
| 10,702,244 B2 | 7/2020 | O'Reilly et al. |
| 10,799,914 B2 | 10/2020 | Savage |
| 10,876,156 B2 | 12/2020 | Weitz et al. |
| 10,888,716 B2 | 1/2021 | Slayton |
| 2002/0086432 A1 | 7/2002 | Tam et al. |
| 2004/0265393 A1 | 12/2004 | Unger et al. |
| 2005/0031499 A1 | 2/2005 | Meier |
| 2006/0013744 A1 | 1/2006 | Mikkelsen et al. |
| 2006/0148064 A1 | 7/2006 | Srivastava |
| 2009/0088669 A1 | 4/2009 | Ido |
| 2010/0004536 A1 | 1/2010 | Rosenberg |
| 2010/0255573 A1 | 10/2010 | Bond et al. |
| 2011/0166551 A1* | 7/2011 | Schafer .............. C12N 13/00 604/522 |
| 2013/0116459 A1 | 5/2013 | Marrone et al. |
| 2015/0056715 A1* | 2/2015 | Laugharn, Jr. ......... C12M 35/04 436/175 |
| 2015/0344868 A1 | 12/2015 | Savage |
| 2016/0202237 A1 | 7/2016 | Zeng et al. |
| 2017/0165506 A1 | 6/2017 | Ortiz et al. |
| 2017/0241878 A1 | 8/2017 | Broyer et al. |
| 2017/0336385 A1 | 11/2017 | Schonbrun et al. |
| 2018/0052147 A1 | 2/2018 | Zeng et al. |
| 2018/0066305 A1 | 3/2018 | Weitz et al. |
| 2018/0106720 A1 | 4/2018 | Schonbrun et al. |
| 2018/0256922 A1 | 9/2018 | Mittelstein et al. |
| 2019/0001154 A1 | 1/2019 | Vortman et al. |
| 2019/0091490 A1 | 3/2019 | Alexander et al. |
| 2019/0185800 A1 | 6/2019 | Weitz et al. |
| 2020/0088717 A1 | 3/2020 | Sacchetti et al. |
| 2020/0222894 A1 | 7/2020 | Bosy et al. |
| 2020/0229793 A1 | 7/2020 | Chen et al. |
| 2020/0355605 A1 | 11/2020 | Causey, III |
| 2020/0375745 A1 | 12/2020 | Sampath et al. |
| 2020/0376302 A1 | 12/2020 | Choi |
| 2020/0405258 A1 | 12/2020 | Dayton et al. |
| 2021/0052802 A1 | 2/2021 | Puskas |
| 2021/0059696 A1 | 3/2021 | Warlick |

FOREIGN PATENT DOCUMENTS

| | | |
|---|---|---|
| EP | 1800743 A1 | 6/2007 |
| EP | 1773977 B1 | 12/2013 |
| EP | 2766188 B1 | 1/2017 |
| EP | 2321643 B1 | 3/2017 |
| EP | 3184624 A1 | 6/2017 |
| EP | 2754493 B1 | 5/2019 |
| EP | 3421090 B1 | 2/2020 |
| EP | 2839035 B1 | 11/2020 |
| WO | WO 03/079006 A1 | 9/2003 |
| WO | WO 2009/134887 A1 | 11/2009 |
| WO | WO 2014/133451 A1 | 9/2014 |
| WO | WO 2018/065626 A1 | 4/2018 |
| WO | WO 2020/041625 A1 | 2/2020 |
| WO | WO 2020/180628 A1 | 9/2020 |
| WO | WO 2020/206281 A1 | 10/2020 |

OTHER PUBLICATIONS

Petersson, Filip, "On acoustic particle and cell manipulation in microfluidic systems", Lund University, Jan. 1, 2007, 88 pages.
Johansson, Linda, "Acoustic Manipulation of Particles and Fluids in Microfluidic Systems", Uppsala University, 2009, 82 pages.
Doria, Arlene et al., "Rapid Blood Plasma Separation with Air-Liquid Cavity Acoustic Transducers", Oct. 2011, 3 pages, Seattle, Washington USA.
Lenshof, A. et al., "Emerging Clinical Applications of Microchip-Based Acoustophoresis", Technology Review, Dec. 2011, 7 pages.
Augustsson, Per et al., "Microfluidic, Label-Free Enrichment of Prostate Cancer Cells in Blood Based on Acoustophoresis", Analytical Chemistry, 2012, 9 pages.
Tojo, Axel, "Free Flow Acoustophoresis: Technology Transfer from Silicon to Glass—Master's Thesis", Lund University, Nov. 2012, 61 pages.
Jakobsson, Ola et al., "Continuous Flow Two-Dimensional Acoustic Orientation of Nonspherical Cells", Analytical Chemistry, 2014, 4 pages.
Laurell, Thomas, "New modalitites for cell separation and microscale diagnostics", Lund University, 2014, 38 pages.
Majedy, Motasam "A microfluidic ultrasonic sample preparation device for bead-based immunoassays", KTH Engineering Sciences, Jun. 3, 2014, 38 pages.
Palmiotti, C.A. et al., "Continuous Acoustic Separation of Blood Components in Plastic Microfluidic Devices", Charles Stark Draper Laboratory, Oct. 2014, 3 pages, San Antonio, Texas, USA.
Antfolk, Maria et al., "A single inlet two-stage acoustophoresis chip enabling tumor cell enrichment from white blook cells", Royal Society of Chemistry, 2015, 8 pages.
Grenvall, Carl et al., "Concurrent Isolation of Lymphocytes and Granulocytes Using Prefocused Free Flow Acoustophoresis", Analytical Chemistry, Jun. 2, 2015, 16 pages.
Jakobsson, Ola et al., "Thousand-Fold Volumetric Concentration of Live Cells with a Recirculating Acoustofluidic Device", Analytical Chemistry, 2015, 6 pages.

(56) References Cited

OTHER PUBLICATIONS

International Search Report and Written Opinion of International Application No. PCT/US2021/029119 dated Aug. 10, 2021.

* cited by examiner

| Absorbance | Transmittance |
|---|---|
| 0 | 1 |
| 0.1 | 0.79 |
| 0.25 | 0.58 |
| 0.5 | 0.32 |
| 0.75 | 0.18 |
| 0.0 | 0.13 |
| 1 | 0.1 |
| 2 | 0.01 |
| 3 | 0.001 |

$T(\lambda) = T_0(\lambda)e^{-ce(\lambda)d}$ $Absorption\ Spectrum = -log\left(\dfrac{T(\lambda)}{T_0(\lambda)}\right)$ $T(T)$ Transmitted Power $T_o(T)$ Incident Before Sample $e(T)$ Extinction Coefficient $d$ Sample's Pathlength (at Specific Wavelength)

ACOUSTOPHORETIC LYSIS DEVICES AND METHODS

CROSS-REFERENCE TO RELATED APPLICATION

This application claims priority to the provisional patent application identified by U.S. Ser. No. 63/016,537 filed Apr. 28, 2020, the entire content of which is hereby expressly incorporated herein by reference.

FIELD OF THE DISCLOSURE

The disclosure generally relates to devices, systems, and methods for testing blood samples. More particularly the disclosure relates to a lysis device configured for lysing red blood cells in a sample vessel by means of ultrasonic acoustic waves, shear forces, pressure, and/or fluid movement, generated in the vessel by an acoustic transducer driven at one or more particular excitation frequency, or range of frequencies. In some non-limiting embodiments, the ultrasonic acoustic waves are generated by a single acoustic transducer. The lysis device may be used in conjunction with blood sample testing analyzers.

BACKGROUND

Point-of-care testing refers generally to medical testing at or near the site of patient care, such as in an emergency room. A desired outcome of such tests is often rapid and accurate lab results to determine a next course of action in the patient care. A number of such point-of-care tests involves analysis of a blood sample from the patient. Many of these tests use whole blood, plasma, or serum.

In some tests, the cell walls of red blood cells in the blood sample are ruptured (lysed) to release hemoglobin. Lysis of the red blood cells may be referred to as hemolysis. Typically, hemolysis was done with chemical or mechanical means.

Some devices lyse the red blood cells using ultrasound. Some point-of-care testing devices use spectrophotometric optical absorption measurement for the determination of the oximetry parameters on a whole blood sample. These devices are fluidic systems that typically position the patient blood sample in a slide cell sample chamber for testing the blood sample. For example, one system described in U.S. Pat. No. 9,097,701 ("Apparatus for Hemolyzing a Blood Sample and for Measuring at Least One Parameter Thereof", issued Aug. 4, 2015) uses two piezo elements, with two balanced resonant elements, surrounding a sample chamber symmetrically, to lyse the red blood cells using acoustophoretic forces. However, these devices are difficult and expensive to manufacture, including requiring a highly precise symmetry with specially made resonant elements.

Once the red blood cells are lysed, the blood samples may then be tested with a spectrophotometer to analyze the intensity of the predetermined wavelengths of light transmitted through a cartridge optical window. A spectrophotometer is an apparatus for measuring the intensity of light in a part of the spectrum, especially as transmitted or emitted by particular substances. The spectrophotometer measures how much a chemical substance absorbs light by measuring the intensity of light as a beam of light passes through the blood sample, or other solution. Each compound in the sample or solution absorbs or transmits light over a particular range of wavelengths.

In such tests, critical-care hematology parameters may be measured that may include hematocrit, free and total hemoglobin, bilirubin, lipids, and oximetry (i.e., E hemoglobin fractions). Doctors and clinicians rely on these measurements to make decisions during patient treatment. These measurements are often performed in a central hematology laboratory on large, complex-to-maintain analyzers. However, obtaining fast, accurate, and precise results in a point-of-care setting is in many ways preferable because it saves time in critical diagnostic situations and avoids specimen transport problems in critical care units. Some blood gas analyzers offer point-of-care capability, but do not present a single solution that provides desired time-to-result, accuracy, precision, and reliability, while being simpler and easier to manufacture than existing devices.

What is needed is a lysis device to provide improved accuracy and precision of measured parameters of a sample within a desired time-to-result at the point of care of a patient, and that is more easily manufactured and with less cost.

SUMMARY

Acoustophoretic lysis devices, methods, and systems are disclosed. The problem of complicated, slow, imprecise, and inaccurate blood sample testing for point-of-care use is addressed through a device configured to lyse red blood cells in a sample vessel by means of ultrasonic acoustic waves, shear forces, pressure, and/or fluid movement, generated in the sample vessel by a single acoustic transducer driven at one or more particular excitation frequency, or range of excitation frequencies.

Consistent with an aspect of the present disclosure, an exemplary lysis device may comprise a sample vessel having an outer surface, a microchannel within the confines of the outer surface, a first port extending through the outer surface to the microchannel, and a second port extending through the outer surface to the microchannel, such that a blood sample is insertable through the first port into the microchannel; wherein the microchannel has a length, a width and a height, and wherein a microchannel aspect ratio of the width to the height is in a range from approximately 0.04 to approximately 0.175; and wherein the sample vessel has a width and a height, and wherein a sample vessel aspect ratio of the width to the height is in a range from approximately 0.5 to approximately 3.0; and an acoustic transducer bonded to the outer surface of the sample vessel to form a monolithic structure, the acoustic transducer configured to generate ultrasonic acoustic standing waves inside the blood sample in the microchannel and configured to bend the sample vessel such that shear forces are induced within the microchannel, the acoustic standing waves and the shear forces causing cavitation in the blood sample thereby rupturing cell walls in the blood sample.

Consistent with an aspect of the present disclosure, an exemplary analyzer may comprise a lysis device, comprising: a sample vessel having an outer surface, a microchannel within the confines of the outer surface, a first port extending through the outer surface to the microchannel, and a second port extending through the outer surface to the microchannel, such that a blood sample is insertable through the first port into the microchannel; wherein the microchannel has a length, a width and a height, and wherein a microchannel aspect ratio of the width to the height is in a range from approximately 0.04 to approximately 0.175; and wherein the sample vessel has a width and a height, and wherein a sample vessel aspect ratio of the width to the height is in a range from approximately 0.5 to approximately 3.0; and an acoustic transducer bonded to the outer surface of the sample vessel to form a monolithic structure, the acoustic transducer configured to generate ultrasonic acoustic standing waves inside the blood sample in the microchannel and configured to bend the sample vessel such that shear forces are induced within the microchannel, the acoustic standing waves and the shear forces causing cavitation in the blood sample thereby rupturing cell walls in the blood sample.

In one implementation, an exemplary analyzer may further comprise an absorbance spectrophotometer comprising a transmitter and a receiver positioned adjacent to the sample vessel, the transmitter positioned to emit a light medium through the microchannel, and a receiver positioned to receive at least a portion of the light medium after the portion of the light medium has passed through the microchannel; a fluidic distribution system having an outlet connected to the first port, and an inlet connected to the second port; and a controller electrically connected to the acoustic transducer and configured to provide electrical signals to the acoustic transducer that when received by the acoustic transducer cause the acoustic transducer to emit ultrasonic acoustic waves and/or cause the acoustic transducer to contract and elongate.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function. In the drawings.

DETAILED DESCRIPTION

Figure 1:
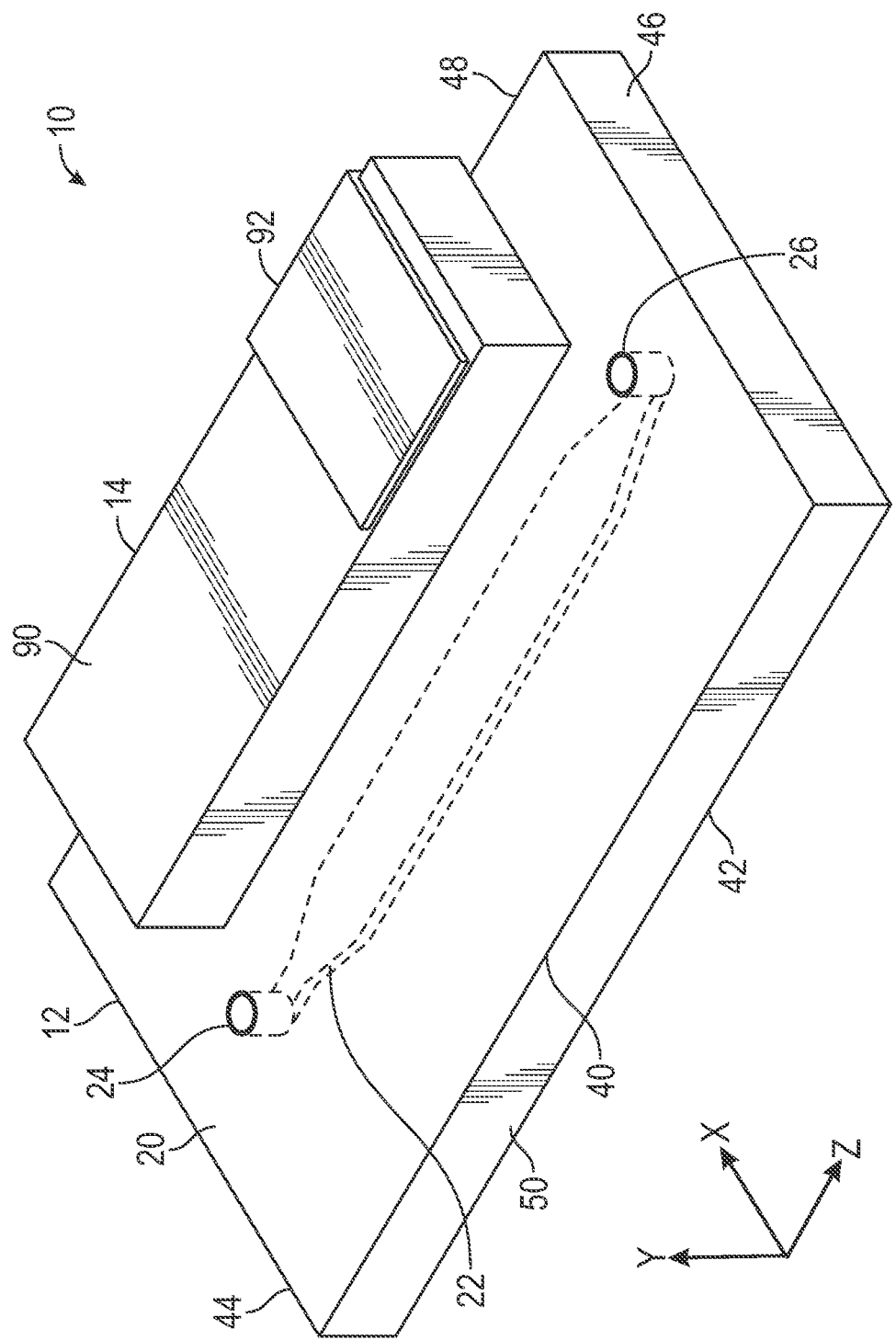
FIG. 1 is a perspective view of an acoustophoretic lysis device in accordance with the present disclosure.
Figure 2:
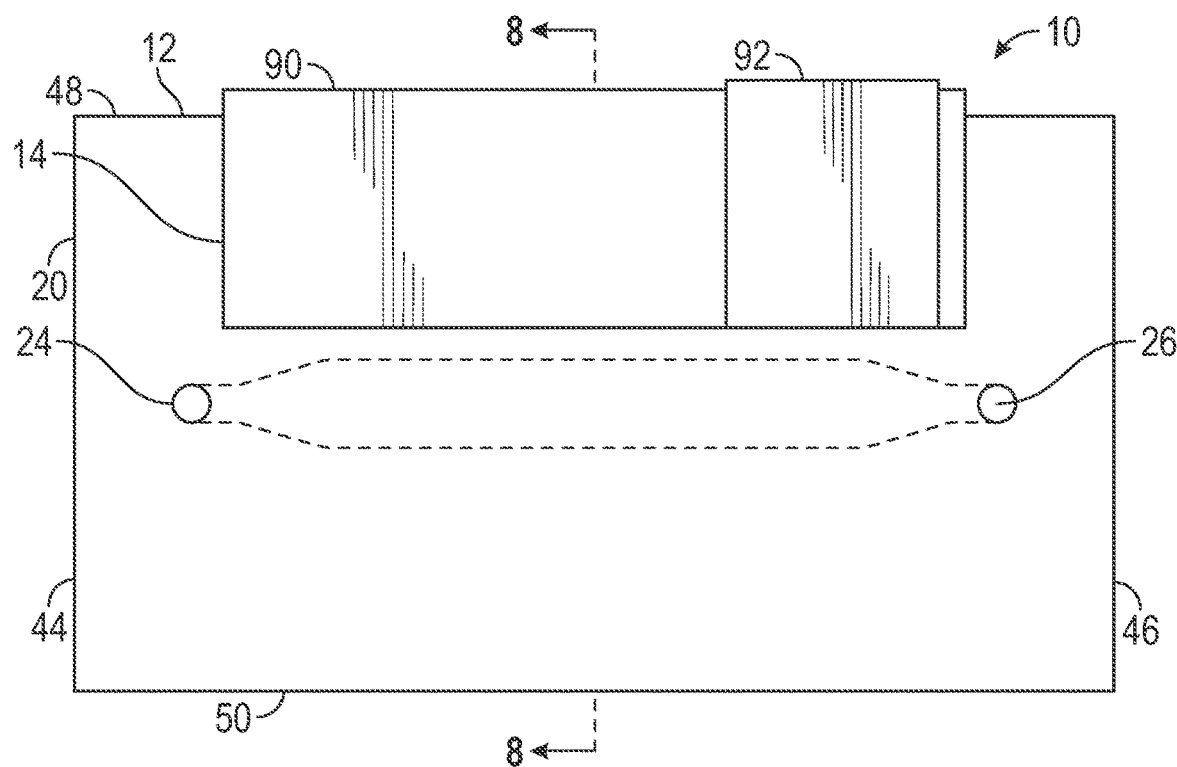
FIG. 2 is a top plan view of an acoustophoretic lysis device in accordance with the present disclosure.
Figure 3:
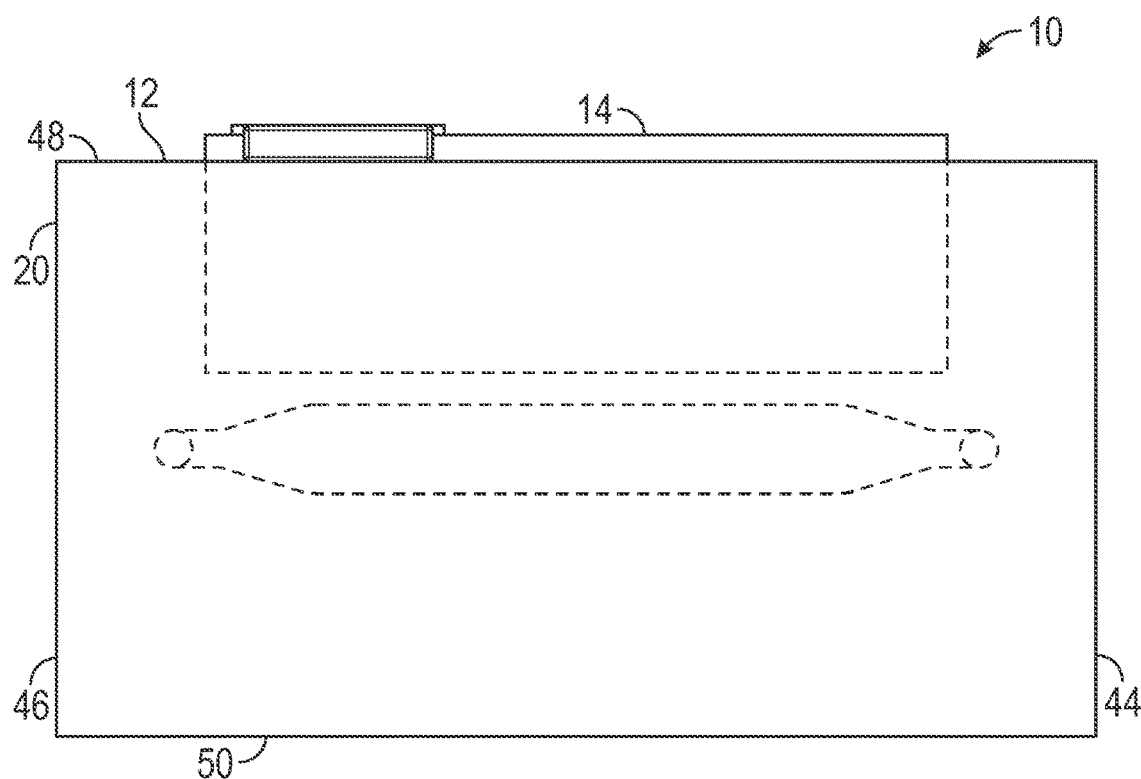
FIG. 3 is bottom plan view of an acoustophoretic lysis device in accordance with the present disclosure.
Figure 4:
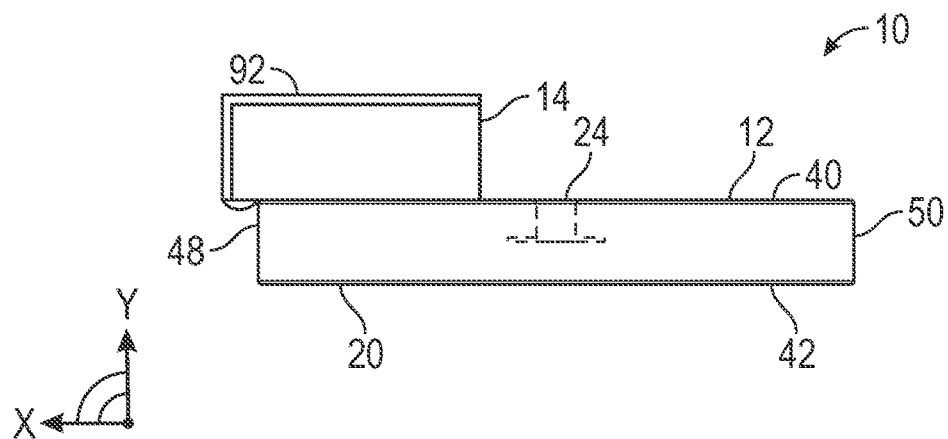
FIG. 4 is a first end elevation view of an acoustophoretic lysis device in accordance with the present disclosure.
Figure 5:
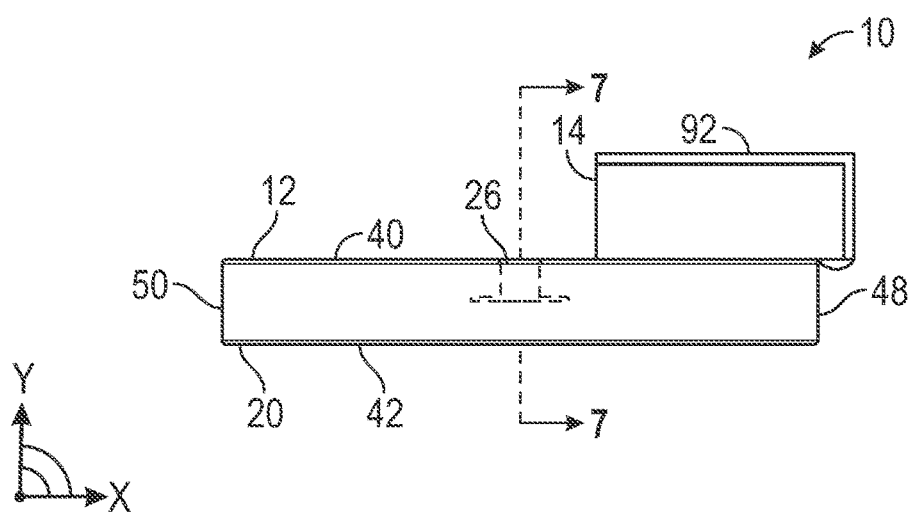
FIG. 5 is a second end elevation view of an acoustophoretic lysis device in accordance with the present disclosure.
Figure 6:
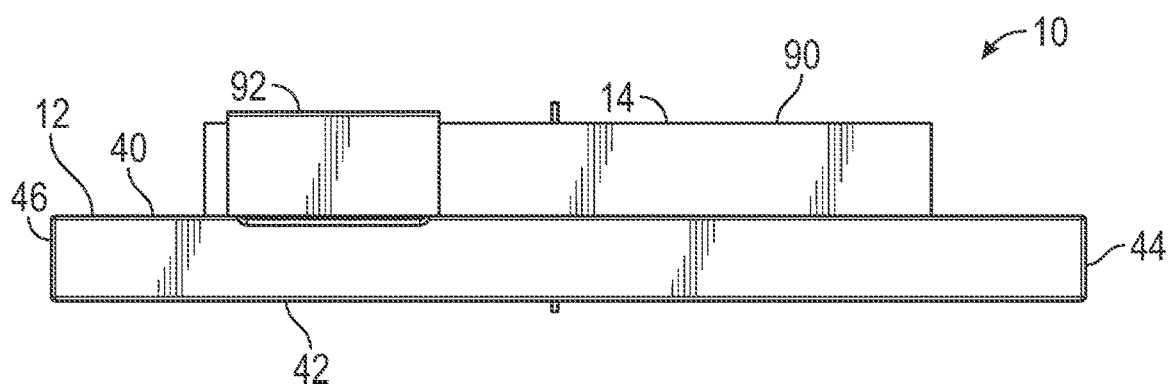
FIG. 6 is a first side elevation view of an acoustophoretic lysis device in accordance with the present disclosure.
Figure 7:
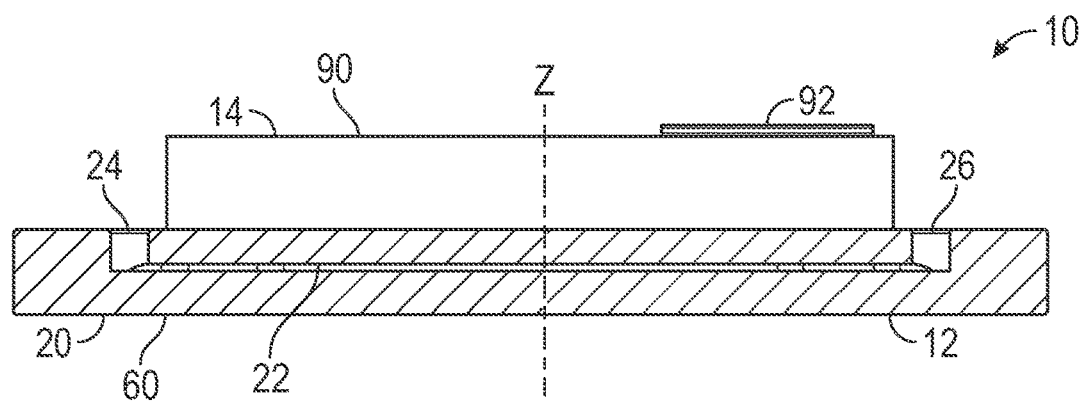
FIG. 7 is a cross-sectional view of an exemplary acoustophoretic lysis device in accordance with the present disclosure.
Figure 8:
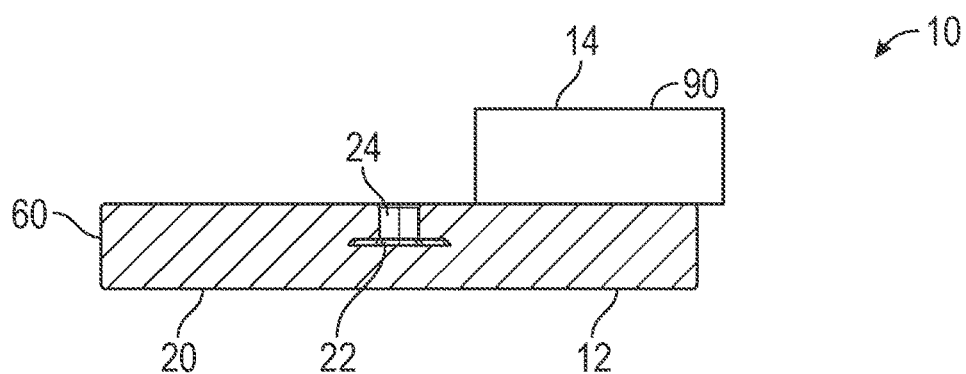
FIG. 8 is a cross-sectional view of an exemplary acoustophoretic lysis device in accordance with the present disclosure.

The following detailed description refers to the accompanying drawings. The same reference numbers in different drawings may identify the same or similar elements.

The mechanisms proposed in this disclosure circumvent the problems described above. The present disclosure describes lysis devices, analyzers, and lysis methods, including a lysis device configured to lyse red blood cells in a sample vessel by means of ultrasonic acoustic waves, shear forces, pressure, and/or fluid movement, generated in the sample vessel by an acoustic transducer connected to the sample vessel and driven at one or more particular excitation frequency, or range of excitation frequencies. In one non-limiting embodiment, the acoustic transducer is a single acoustic transducer. The present disclosure further describes an analyzer configured to receive and interact with the lysis device for testing a sample in the sample vessel, as well as a method of use.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Further, use of the term "plurality" is meant to convey "more than one" unless expressly stated to the contrary.

As used herein, qualifiers like "about," "approximately," and combinations and variations thereof, are intended to include not only the exact amount or value that they qualify, but also some slight deviations therefrom, which may be due to manufacturing tolerances, measurement error, wear and tear, stresses exerted on various parts, and combinations thereof, for example.

As used herein, the term "substantially" means that the subsequently described parameter, event, or circumstance completely occurs or that the subsequently described parameter, event, or circumstance occurs to a great extent or degree. For example, the term "substantially" means that the subsequently described parameter, event, or circumstance occurs at least 90% of the time, or at least 91%, or at least 92%, or at least 93%, or at least 94%, or at least 95%, or at least 96%, or at least 97%, or at least 98%, or at least 99%, of the time, or means that the dimension or measurement is within at least 90%, or at least 91%, or at least 92%, or at least 93%, or at least 94%, or at least 95%, or at least 96%, or at least 97%, or at least 98%, or at least 99%, of the referenced dimension or measurement.

The use of the term "at least one" or "one or more" will be understood to include one as well as any quantity more than one. In addition, the use of the phrase "at least one of X, V, and Z" will be understood to include X alone, V alone, and Z alone, as well as any combination of X, V, and Z.

The use of ordinal number terminology (i.e., "first", "second", "third", "fourth", etc.) is solely for the purpose of differentiating between two or more items and, unless explicitly stated otherwise, is not meant to imply any sequence or order or importance to one item over another or any order of addition.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As discussed above, typical previous devices for blood sample testing for point-of-care use are complicated, slow, imprecise, and inaccurate. The present disclosure addresses these deficiencies with devices, systems, and methodology for lysing red blood cells in a sample vessel by means of ultrasonic acoustic waves, shear forces, pressure, and/or fluid movement, generated in the sample vessel by a single acoustic transducer connected to the sample vessel and driven at one or more particular excitation frequency, or range of excitation frequencies.

Referring now to the drawings, and in particular to FIGS. 1-8, an acoustophoretic lysis device 10 is shown. In general, the lysis device 10 comprises a sample vessel 12 and an acoustic transducer 14 bonded to the sample vessel 12. In one embodiment, the lysis device 10 is a monolithic structure, such as that formed by the sample vessel 12 and the acoustic transducer 14 bonded together using a suitable bonding material, such as epoxy.

The sample vessel 12 has an outer surface 20, a microchannel 22 within the confines of the outer surface 20, a first port 24 extending through the outer surface 20 to the microchannel 22 and in fluid communication with the microchannel 22, and a second port 26 extending through the outer surface 20 to the microchannel 22 and in fluid communication with the microchannel 22. In one embodiment, the outer surface 20 may have a mounting area for the acoustic transducer 14.

In one embodiment, the sample vessel 12 has a top 40, a bottom 42, a first end 44, a second end 46, a first side 48, and a second side 50, wherein the first side 48 and the second side 50 extend between the first end 44 and the second end 46 and between the top 40 and the bottom 42. In one embodiment, the top 40 and the bottom 42 are planar. In one embodiment, the first side 48 and the second side 50 are planar. In one embodiment, the first end 44 and the second end 46 are planar. In one embodiment, the top 40, the bottom 42, the first end 44, the second end 46, the first side 48, and the second side 50 cooperate to form a three-dimensional rectangular cuboid.

The sample vessel 12 may be partially, substantially, or completely transparent. In one embodiment, the sample vessel 12 is transparent at least above and below the microchannel 22, such that a medium such as light may pass through the sample vessel 12 through the microchannel 22, interact with any substance within the microchannel 22, and pass out of the sample vessel 12.

The sample vessel 12 may be constructed of glass. In one embodiment, the sample vessel 12 may be constructed of a material (glass or non-glass) having a Young's modulus within a range from about 50 Gpa to about 90 Gpa. The material property known as Young's modulus, or the modulus of elasticity, is a measure of the ability of the material to withstand changes in length when under lengthwise tension or compression. Young's modulus is equal to the longitudinal stress divided by the strain. In one embodiment, the sample vessel 12 may be constructed of plastic with a rigidity and/or Young's modulus similar to that of glass. In one embodiment, the sample vessel 12 may be constructed from alkali borosilicate glass. One example of alkali borosilicate glass is made by Schott Advanced Optics, located at 400 York Avenue, Duryea, Pa. 18642, and marketed under the name "D 263 T ECO Thin Glass."

The sample vessel 12 has a length from the first end 44 to the second end 46, a width from the first side 48 to the second side 50, a thickness between the top 40 and the bottom 42, and an aspect ratio defining the proportional relationship between the length and the width. The sample vessel 12 has a longitudinal axis along the length and a latitudinal axis along the width.

In one embodiment, the aspect ratio of the sample vessel 12 is in a range from approximately 0.5 to approximately 3.0. In one embodiment, the aspect ratio of the sample vessel 12 is in a range from approximately 1.4 to approximately 1.9. In one embodiment, the length may be approximately twenty-two millimeters and the width may be approximately twelve millimeters. In one embodiment, the length may be approximately seventeen millimeters and the width may be approximately twelve millimeters. In one embodiment, the length may be approximately seventeen millimeters and the width may be approximately six millimeters. In one embodiment, the length may be approximately twelve millimeters and the width may be approximately six millimeters.

The microchannel 22 may be configured to receive a fluidic sample 52 (including, but not limited to, a blood sample, a "blank" sample, and/or a washing solution sample) through the first port 24 and/or the second port 26. The microchannel 22 has a length, a width, and a height. Typically, the length of the microchannel 22 is oriented along the longitudinal axis of the sample vessel 12 and the width of the microchannel 22 is oriented along the latitudinal axis of the sample vessel 12. However, it will be understood that the microchannel 22 may be oriented at an angle from or offset from the longitudinal axis and/or the latitudinal axis of the sample vessel 12.

The microchannel 22 has an aspect ratio defining the proportional relationship between the width and the height of the microchannel 22. In one embodiment, the width to height aspect ratio of the microchannel 22 is in a range from approximately 0.04 to approximately 0.175. In one embodiment, the width to height aspect ratio of the microchannel 22 is in a range from approximately 0.04 to approximately 0.125. In one embodiment, the width to height aspect ratio of the microchannel 22 is approximately 0.05.

In one embodiment, the width of the microchannel 22 is about two millimeters. In one embodiment, the width of the microchannel 22 is greater than an illumination width of a light yield area of the absorbance spectrophotometer 102. An illumination width may be defined as the width of a cross-section of the light yield along an optical pathway from the absorbance spectrophotometer 102 where the optical pathway intersects the microchannel 22. For example, when the illumination diameter is between 1 millimeter and 1.5 millimeter, then the width of the microchannel 22 may be at least approximately 1.6 millimeters. The width of the microchannel 22 may be determined to allow for adequate mechanical alignment between the microchannel 22 and optical pathway. For example, for an illumination width between 1 millimeter and 1.5 millimeter, the width of the microchannel 22 may be approximately two millimeters.

In one embodiment, the length of the microchannel 22 may be between approximately ten millimeters and approximately twelve millimeters. In one embodiment, the length of the microchannel 22 may be at least approximately four millimeters. In one embodiment, the length of the microchannel 22 may be between approximately four millimeters and approximately twenty millimeters.

In one embodiment, the length of the microchannel 22 may be based at least in part on a predetermined desired number of acoustic nodes to be created in the microchannel 22. For example, for a microchannel 22 having a width of approximately two millimeters and where a whole blood wave propagation speed is approximately 1500 m/s, a calculated single acoustic node is at 350 kHz. The acoustic nodes may be distributed in the microchannel 22 evenly spaced along the length of the microchannel 22 (for example, 2×2 mm=4 mm), where high pressure creates a uniform distribution of lysed blood. For example, if the predetermined desired number of acoustic nodes is five nodes on each side wall of the microchannel 22 (see FIG. 13), then the length of the microchannel 22 may be set at approximately seventeen millimeters.

The height of the microchannel 22 can vary, as discussed below. The height of the microchannel 22 may be based on the amount of absorption in lysed blood of the light yield from the absorbance spectrophotometer 102 and the desired precision of the absorption. For example, the desired absorption may be at approximately 1 Optical Density (OD).

In one embodiment, the height of the microchannel 22 is about 100 micrometers. In one embodiment, the height of the microchannel 22 is about 150 micrometers. In one embodiment, the height of the microchannel 22 is about 250 micrometers. In one embodiment, the height of the microchannel 22 is about 300 micrometers. In one embodiment, the height of the microchannel 22 is between approximately 80 micrometers and approximately 300 micrometers. In one embodiment, the height of the microchannel 22 is between approximately 80 micrometers and approximately 150 micrometers.

The first port 24 and the second port 26 are fluidly connected to the microchannel 22 and extend from the microchannel 22 through the outer surface 20 of the sample vessel 12. In one embodiment, the first port 24 is fluidly connected to the microchannel 22 and may extend from the microchannel 22 to the top 40, the bottom 42, the first end 44, the second end 46, the first side 48, and/or the second side 50 of the sample vessel 12. In one embodiment, the second port 26 is fluidly connected to the microchannel 22 and may extend from the microchannel 22 to the top 40, the bottom 42, the first end 44, the second end 46, the first side 48, and/or the second side 50 of the sample vessel 12. The first port 24 and the second port 26 may extend to the same or to different ones of the top 40, the bottom 42, the first end 44, the second end 46, the first side 48, and/or the second side 50.

In one embodiment, the first port 24 and the second port 26 each have a diameter of between approximately 0.5 millimeter (500 micrometers) and approximately 1.5 millimeter (1500 micrometers). In one embodiment, the first port 24 and the second port 26 each have a diameter of approximately 0.8 millimeter (800 micrometers).

The sample vessel 12 may be a monolithic fabrication, either in that the sample vessel 12 is formed from a single piece of material or in that the sample vessel 12 is formed from a plurality of pieces that are interconnected to form a unified whole.

As shown in FIGS. 4-8, in one embodiment, the sample vessel 12 may comprise a single substrate 60 bound by the outer surface 20 and having the microchannel 22 within the single substrate 60 and the first port 24 and the second port 26 fluidly connected to the microchannel 22 and extending to the outer surface 20. For example, the sample vessel 12 may be a 3D printed glass substrate. The 3D printed substrate may be printed to include the microchannel 22, the first port 24, and the second port 26.

Figure 9:
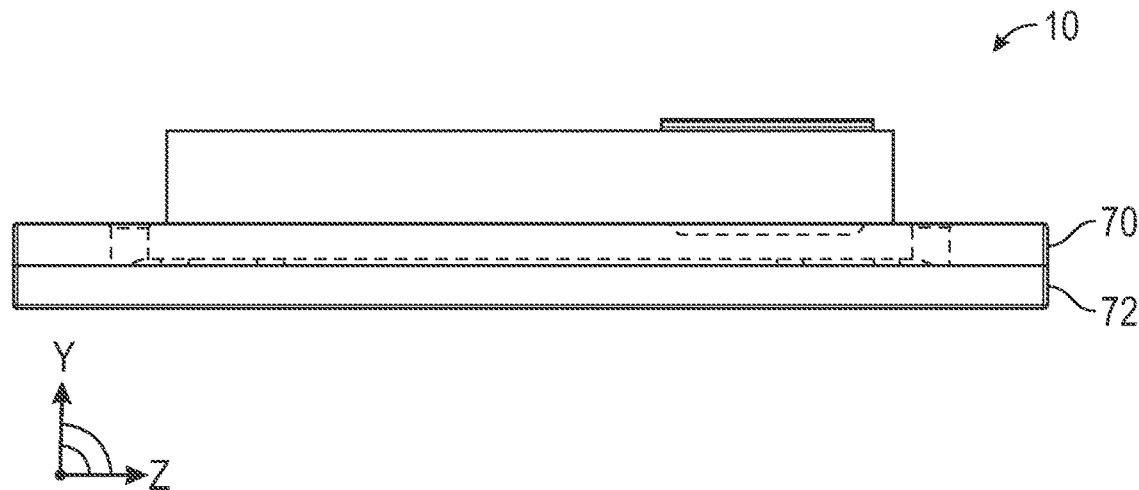
FIG. 9 is a first side elevation view of another exemplary acoustophoretic lysis device in accordance with the present disclosure.

As illustrated in FIG. 9, in one embodiment, the sample vessel 12 may comprise a first substrate 70 and a second substrate 72. The second substrate 72 may be layered with the first substrate 70 so as to form a monolithic structure. In one embodiment, the first substrate 70 and the second substrate 72 may be annealed to one another. In one embodiment, the first substrate 70 and the second substrate 72 may be thermal-plasma bonded to one another. In one embodiment, the first substrate 70 and the second substrate 72 have the same length to width aspect ratio as the sample vessel 12.

The microchannel 22 may be positioned in the first substrate 70, the second substrate 72, and/or be formed partially in the first substrate 70 and partially in the second substrate 72. In one embodiment, the microchannel 22, the first port 24, and the second port 26 are positioned in the first substrate 70. In one embodiment, the microchannel 22 is etched into the first substrate 70 and/or the second substrate 72. In one embodiment, the microchannel 22 is positioned in the first substrate 70 and one or both of the first port 24 and the second port 26 is positioned in the second substrate 72. One or both of the first port 24 and the second port 26 may be positioned in (and/or extend through) the first substrate 70 and/or the second substrate 72.

Figure 10:
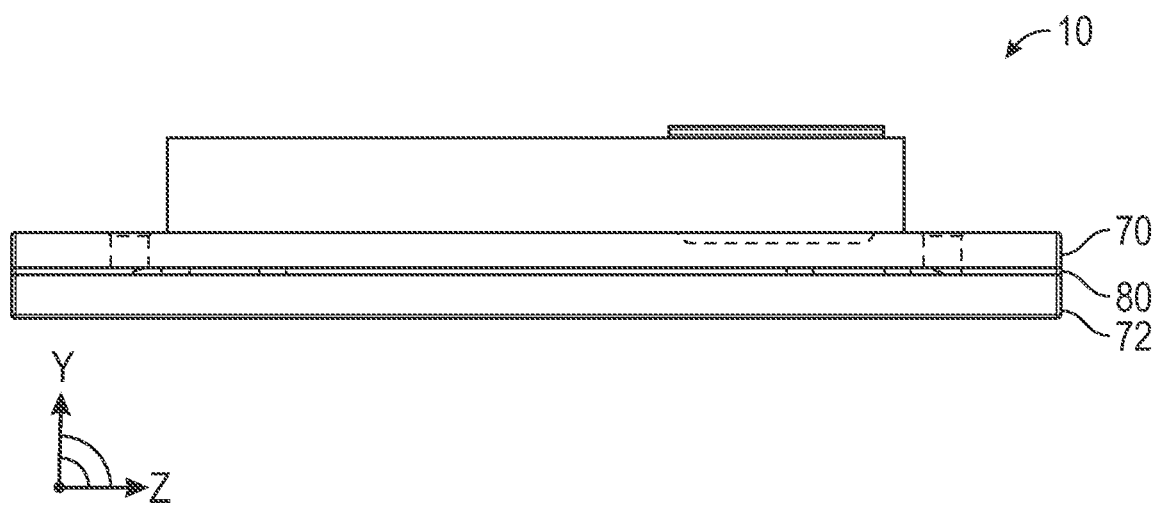
FIG. 10 is a first side elevation view of yet another exemplary acoustophoretic lysis device in accordance with the present disclosure.
Figure 11:
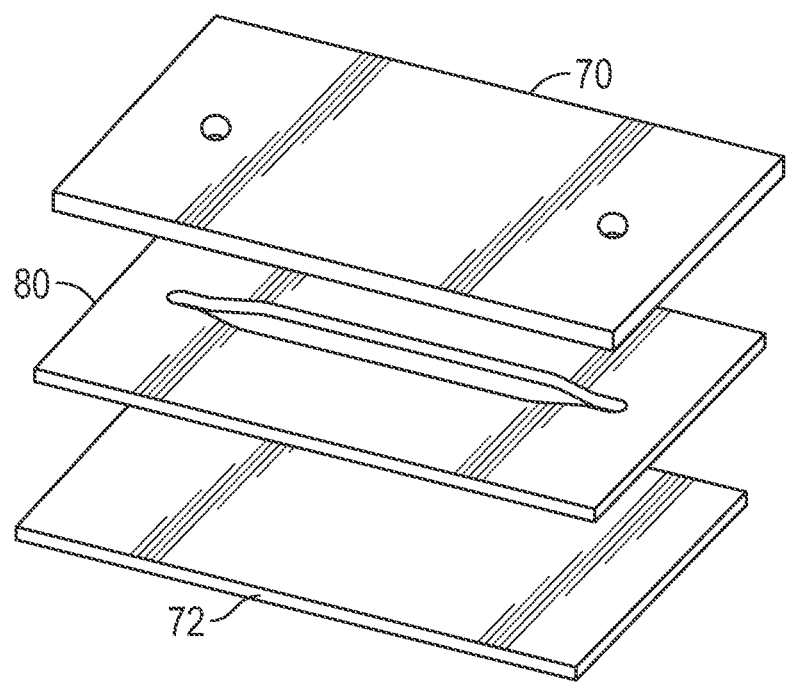
FIG. 11 is a perspective view of components of an exemplary sample vessel in accordance with the present disclosure.

As illustrated in FIGS. 10 and 11, in one embodiment, the sample vessel 12 may comprise the first substrate 70, the second substrate 72, and a third substrate 80 between the first substrate 70 and the second substrate 72. The first substrate 70, the second substrate 72, and the third substrate 80 may be layered so as to form a monolithic structure. In one embodiment, the first substrate 70, the second substrate 72, and the third substrate 80 may be thermal-plasma bonded to one another. In one embodiment, the first substrate 70, the second substrate 72, and the third substrate 80 may be annealed to one another. One or both of the first port 24 and the second port 26 may be positioned in the first substrate. The microchannel 22 may be positioned in the second substrate 72. In one embodiment, the microchannel 22 is a slot positioned through the third substrate 80. In one embodiment, the third substrate 80 may have the same thickness as the height of the microchannel 22. In one embodiment, the third substrate 80 may be 100 micrometers thick.

Returning to FIG. 1, the acoustic transducer 14 is mounted to the sample vessel 12 (such as to the mounting area of the outer surface 20) to form the monolithic structure of the lysis device 10. The acoustic transducer 14 may have a mounting area that mounts to the mounting area of the outer surface 20. In one embodiment, the acoustic transducer 14 is mounted at least partially to the top 40 of the sample vessel 12; however, it will be understood that the acoustic transducer 14 may be mounted to the top 40, the bottom 42, the first end 44, the second end 46, the first side 48, and/or the second side 50. The acoustic transducer 14 is positioned in relation to the microchannel 22 such that it does not block light from moving through the microchannel 22 from the top or the bottom of the sample vessel 12. The acoustic transducer 14 may be offset from the microchannel 22 such that the acoustic transducer 14 allows light to enter the microchannel 22 from outside of the sample vessel 12. In one embodiment, the acoustic transducer 14 has a length and has a longitudinal axis along the length that is orientated substantially parallel to the longitudinal axis of the sample vessel 12. In one embodiment, the acoustic transducer 14 has a width that is smaller than the length of the acoustic transducer 14.

The acoustic transducer 14 may be positioned on the opposite side from one or both of the first port 24 and the second port 26 or on the same side as one or more of the first port 24 and the second port 26 on the sample vessel 12

The acoustic transducer 14 may be bonded to the sample vessel 12. The bond may be thin relative to a thickness of the acoustic transducer 14 and the sample vessel 12. The acoustic transducer 14 may be bonded to the sample vessel 12 with an adhesive. The adhesive may be configured to allow acoustic wave propagation with low losses of acoustic waves. In one embodiment, a liquid adhesive may be applied to the acoustic transducer 14 and then the acoustic transducer 14 may be attached via the liquid adhesive to the sample vessel 12. For example, a liquid adhesive having temperature stability up to 350° C., excellent adhesive force on glass, and high hardness (rigidity) may be applied. In one example, the liquid adhesive may be an epoxy glue, such as EPO-TEK 353ND (made by Epoxy Technology, Inc., located at 14 Fortune Drive, Billerica, Mass.), which allows for ultrasound propagation and which has a shore D hardness of about 85. In one example, approximately 5 μl of liquid adhesive may be applied. The acoustic transducer 14 may be clamped to the sample vessel 12 and the adhesive cured at approximately 150° C. In one implementation, after curing, the thickness of the adhesive may be approximately 100 μm.

The acoustic transducer 14 may be configured to convert an electrical charge into another form of energy, such as sound waves having one or more frequency and/or a range of frequencies. The acoustic transducer 14 may be configured to oscillate when alternating current is applied to the acoustic transducer 14, thereby creating the sound waves that are introduced into the sample vessel 12, which may create one or more acoustic node within the blood sample 52 in the sample vessel 12. As shown in FIG. 1, the acoustic transducer 14 may comprise a first electrode 90 and a second electrode 92 configured to connect with an alternating current source. In one embodiment, the acoustic transducer 14 may be a piezoelectric ultrasonic transducer.

Figure 12:
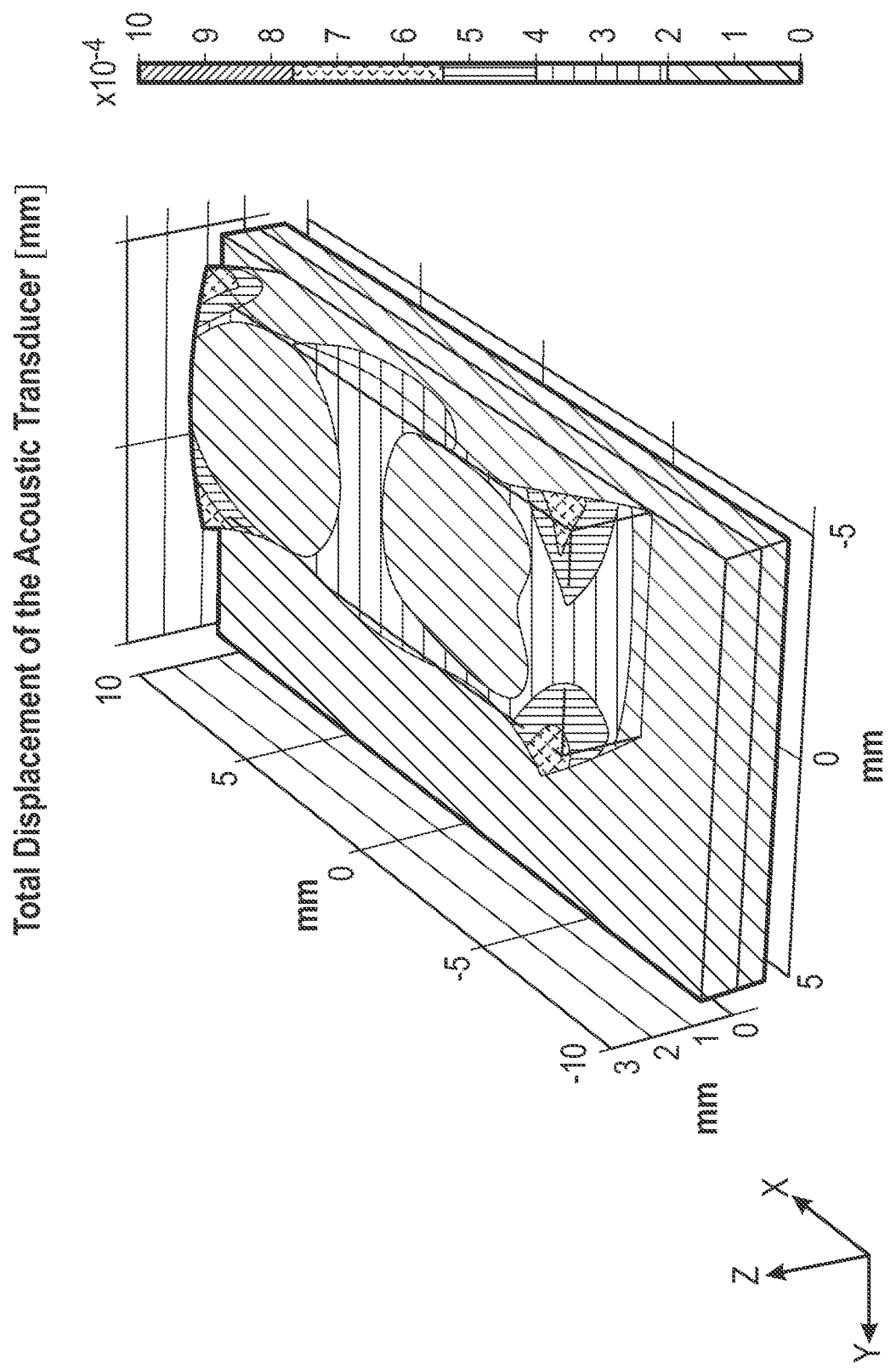
FIG. 12 is a graphical representation of total displacement of an exemplary lysis device in accordance with the present disclosure.

The acoustic transducer 14 may be configured to generate ultrasonic activity, producing sound waves with frequencies, by expanding and contracting when electrical frequency and voltage is applied. FIG. 12 shows a graphical representation of one example of the total displacement of the acoustic transducer 14 in one exemplary operation of the acoustic transducer 14.

In one embodiment, the acoustic transducer 14 may be configured to produce ultrasonic sound waves having a resonant frequency that causes resonances in a blood sample 52 in the microchannel 22 of the sample vessel 12 such that walls of red blood cells in the blood sample 52 are ruptured. In one embodiment, the acoustic transducer 14 may be configured to produce ultrasonic sound waves (which may also be referred to herein as ultrasonic acoustic waves) having a resonant frequency that causes cavitation in the blood sample 52, thereby rupturing the walls of the red blood cells. In one embodiment, the acoustic transducer 14 has a first resonant frequency and the monolithic structure of the lysis device 10 has a second resonant frequency spaced spectrally from the first resonant frequency, the second resonant frequency being a frequency of sound waves that is generated by the acoustic transducer 14 and introduced into the sample vessel 12 thereby causing cavitation in the blood sample 52, thereby rupturing the walls of the red blood cells.

Figure 13:
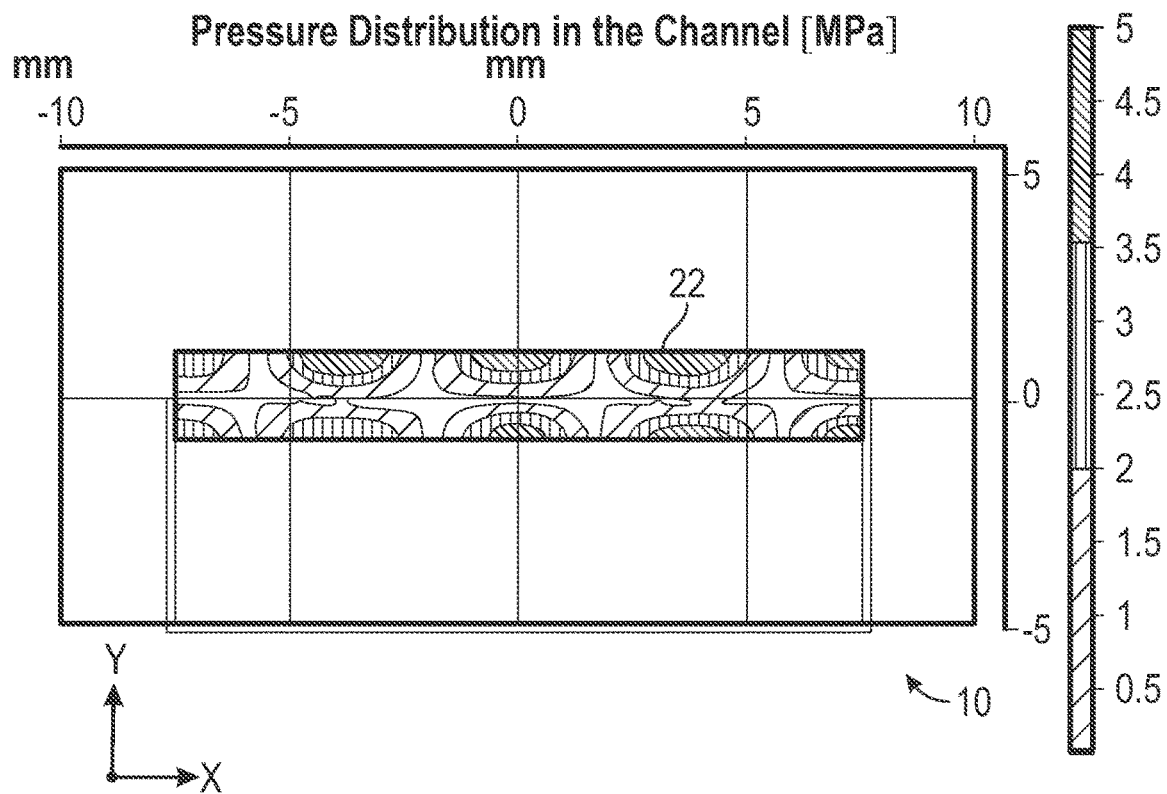
FIG. 13 is a plan view of pressure distribution in a microchannel of an exemplary sample vessel in accordance with the present disclosure.
Figure 14:
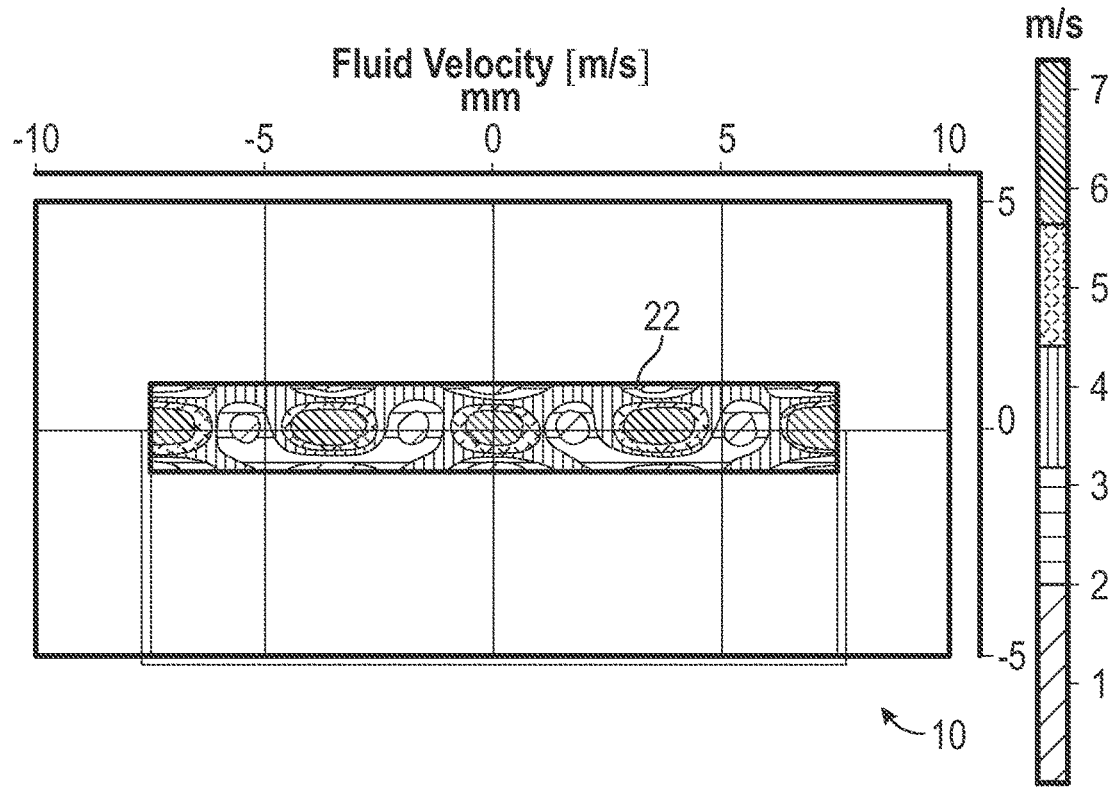
FIG. 14 is a plan view of fluid velocity in a microchannel of an exemplary sample vessel in accordance with the present disclosure.
Figure 15:
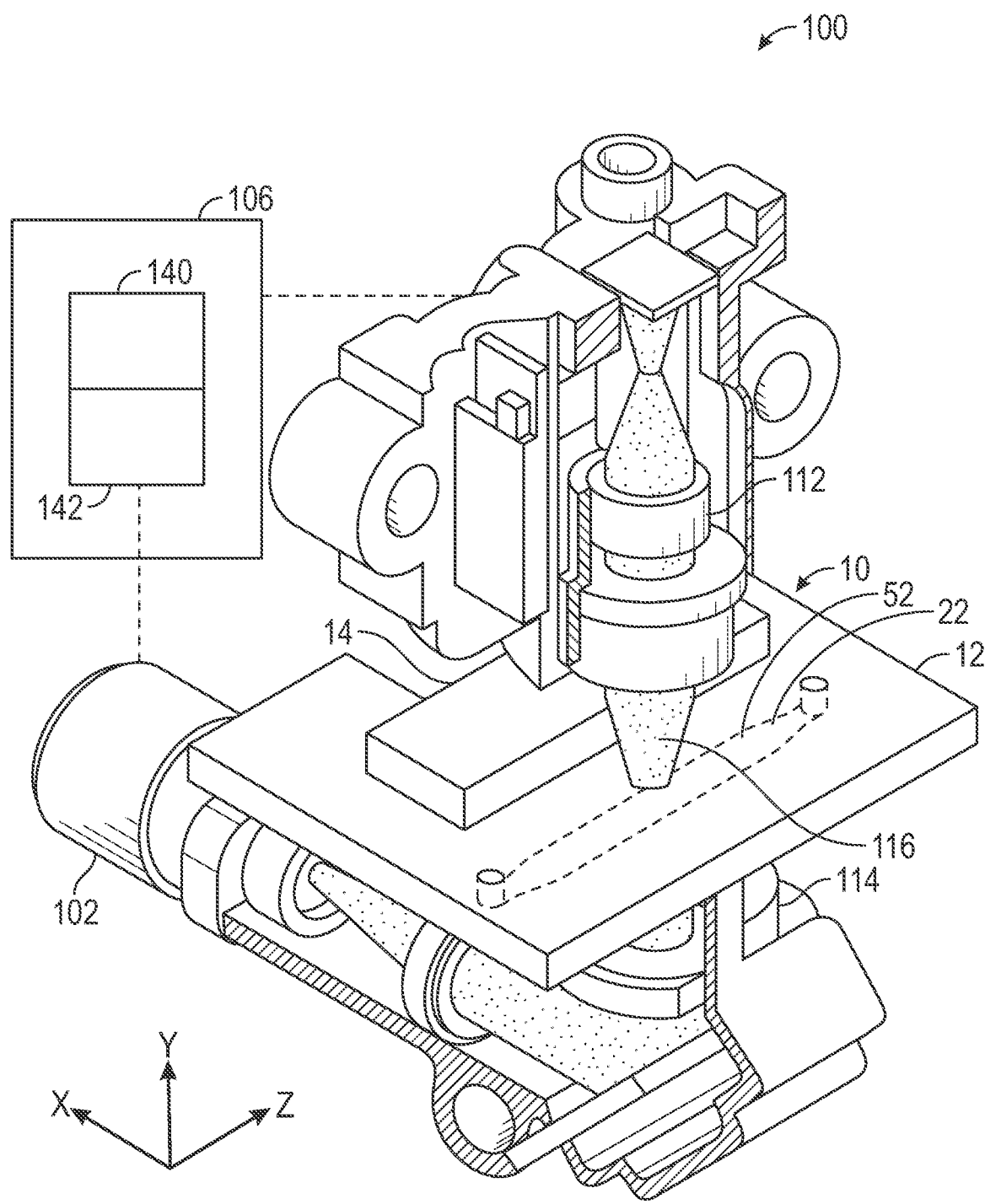
FIG. 15 is a perspective view of an exemplary analyzer in accordance with the present disclosure.

In one embodiment, the second resonant frequency may cause one or more acoustic standing wave, which may form in regions (referred to as nodes) having approximately zero force and approximately no particle movement and the highest hydraulic pressure in the microchannel 22, inside the microchannel 22 of the sample vessel 12 such that walls of red blood cells in the blood sample 52 are ruptured, as illustrated in FIGS. 13 and 14. An acoustic standing wave, also known as a stationary wave, is a wave that oscillates in time, but that has a peak amplitude profile that does not move in space.

In one example, at the main resonance of the acoustophoretic lysis device 10 (that is, the sample vessel 12 bonded to the acoustic transducer 14), for example, when the sample vessel 12 is made of glass, the microchannel 22 has a width of approximately two millimeters with an aspect ratio of 0.05 to 0.125, and the sample vessel 12 has a width of approximately twelve millimeters with an aspect ratio of 1.4 to 1.9, the acoustic transducer 14 may be configured to produce ultrasonic sound waves in the range of 330 kHz to 350 kHz with peak pressure within the microchannel 22 of five MPa (see FIG. 13), and peak velocity up to eight m/s (see FIG. 14). One exemplary case of the pressure distribution (FIG. 13) and the fluid velocity (FIG. 14) of the blood sample 52 in the microchannel 22 when the acoustic transducer 14 is activated is illustrated in FIGS. 13 and 14.

However, ultrasonic sound waves inside the microchannel 22 and the ultrasonic acoustic transducer 14 may produce undesired heat, including undesired heat in the blood sample 52 in the microchannel 22. To avoid any overheating of the blood sample 52, the acoustic transducer 14 may be operated to produce a resonant frequency for a predetermined period of time. For example, the acoustic transducer 14 may be operated to generate sound waves having the second resonant frequency for between approximately one second and approximately two seconds. In one embodiment, the acoustic transducer 14 may be operated to generate sound waves having the second resonant frequency for less than approximately one and a half seconds. In one example, the lysis device 10 may be configured to operate the acoustic transducer 14 for equal to or less than 1.5 seconds to result in 99.99% red blood cell lysis. In one example, the lysis device 10 may be configured to operate the acoustic transducer 14 for approximately ten seconds or less.

In one embodiment, the ultrasonic sound waves inside the microchannel 22 disrupt the blood cells and cell walls into fine particles which produce less light scattering during optical measurement of the blood sample 52 than larger particles.

In one embodiment, the acoustic transducer 14 may be configured to produce ultrasonic sound waves in a range of frequencies and the second resonant frequency may be within the range of frequencies.

In one embodiment, the acoustic transducer 14 may be configured to produce ultrasonic sound waves in a range of frequencies that is greater than approximately 300 kHz.

The resonant frequency, and/or the frequency range, may be determined based on one or more factors including the size, shape, and material of the sample vessel 12; the size and shape of the microchannel of the sample vessel 12; the amount of fluid in the fluidic sample 52; and/or the size, shape, and material of the acoustic transducer 14.

For example, when the sample vessel 12 is made of glass, the microchannel 22 has an aspect ratio of approximately 0.05 to approximately 0.125, and the sample vessel 12 has an aspect ratio of approximately 1.4 to approximately 1.9, the acoustic transducer 14 may be configured to produce ultrasonic sound waves in the range of approximately 330 kHz to approximately 350 kHz.

The width of the microchannel 22 may be determined based at least on acoustic wave propagation speed inside the blood sample 52 (for example, approximately 1500 m/s) and using the predetermined desired number of acoustic nodes as one node in the middle of the microchannel 22, such that the frequency is approximately 330 kHz to approximately 350 kHz. The following formula may be used to determine, at least in part, a first acoustic node inside the microchannel 22 (with an exemplary 2000 m width and 100 m depth), without considering any minor reflection or other mirroring:

$$2f = v/\lambda$$

where f is the frequency, v the wave speed in fluid and A the wavelength (where the wavelength is ½ of the width of the microchannel 22).

Because the resonant frequency of the sample vessel 12 may be difficult to calculate precisely due to manufacturing and/or material variances, in one embodiment, the acoustic transducer 14 may be configured to sweep the frequency within a frequency range having a plurality of frequencies, starting at a first frequency and proceeding through one or more second frequencies to a third frequency of the plurality of frequencies. In one embodiment, the acoustic transducer 14 may be configured to sweep the frequency range in steps, such as steps of one kHz of frequency. In one embodiment, sweeping the frequency range from the first frequency to the third frequency ensures that the resonant frequency for the lysis device 10 plus the blood sample 52 is reached, even in light of variances in the geometry and materials of the lysis device 10.

In one embodiment, the acoustic transducer 14 may be configured to sweep the frequency range between approximately 330 kHz and approximately 350 kHz, such as, in approximately one kHz steps. The acoustic transducer 14 may be configured to sweep the frequency range starting approximately 330 kHz and going to approximately 350 kHz and/or the acoustic transducer 14 may be configured to sweep the frequency range starting approximately 350 kHz and going to approximately 330 kHz, for example.

In one embodiment, the acoustic transducer 14 may be configured to sweep the frequency range over a time period greater than zero seconds, and less than five seconds, less than four seconds, less than three seconds, less than two seconds, and/or less than one second. In one embodiment, the acoustic transducer 14 may be configured to sweep the frequency range in a time period between approximately one and approximately two seconds.

In one embodiment, additionally or alternatively, the lysis device 10 may lyse the blood cells in the blood sample 52 by inducing shear and bending modes in the microchannel 22 of the sample vessel 12. Displacement of the rigid bonded ultrasonic acoustic transducer 14, which may be primarily transverse displacement, causes vibration and movement of the sample vessel 12 bonded to the acoustic transducer 14. When activated, the ultrasonic acoustic transducer 14 changes shape, contracting and elongating (transverse displacement) as shown in FIG. 12. The movement of the ultrasonic acoustic transducer 14, is translated to the sample vessel 12, changing the geometry and/or volume of the microchannel 22, which induces shear and bending in the microchannel 22 of the sample vessel 12. FIG. 12 shows a graphical representation of one example of the total displacement of the acoustic transducer 14 in one exemplary operation of the acoustic transducer 14.

The displacement of the acoustic transducer 14 may result in bending of, and shear forces within, the sample vessel 12, which subsequently may cause and/or contribute to lysis of the blood sample 52 in the microchannel 22 of the sample vessel 12 due to a combination of high pressure, shear forces, and/or fluid movement inside the microchannel 22. Therefore, in some implementations, lysis of the blood sample 52 in the microchannel 22 may be caused by a combination of acoustic standing waves, pressure, shear forces, and/or fluid movement within the blood sample 52.

Shear stress may be developed at the bond between the piezoelectric acoustic transducer 14 and the sample vessel 12 when the acoustic transducer 14 is activated. The shear stress may result in high pressures inside of the microchannel 22. For example, in one embodiment, a preferred high pressure may be approximately 5 MPa. In one embodiment, the pressure may be in a range of approximately 3 MPa to approximately 7 MPA. The level of pressure may be controlled by the level of contraction/elongation of the acoustic transducer 14, which may depend on the electric field strength of the acoustic transducer 14.

The combination of acoustic standing waves inside the microchannel 22 along with shear and/or bending of the sample vessel 12 causes significant cavitation in the whole blood sample 52 in the microchannel 22, which causes the rupture of the cell walls.

Figure 21:
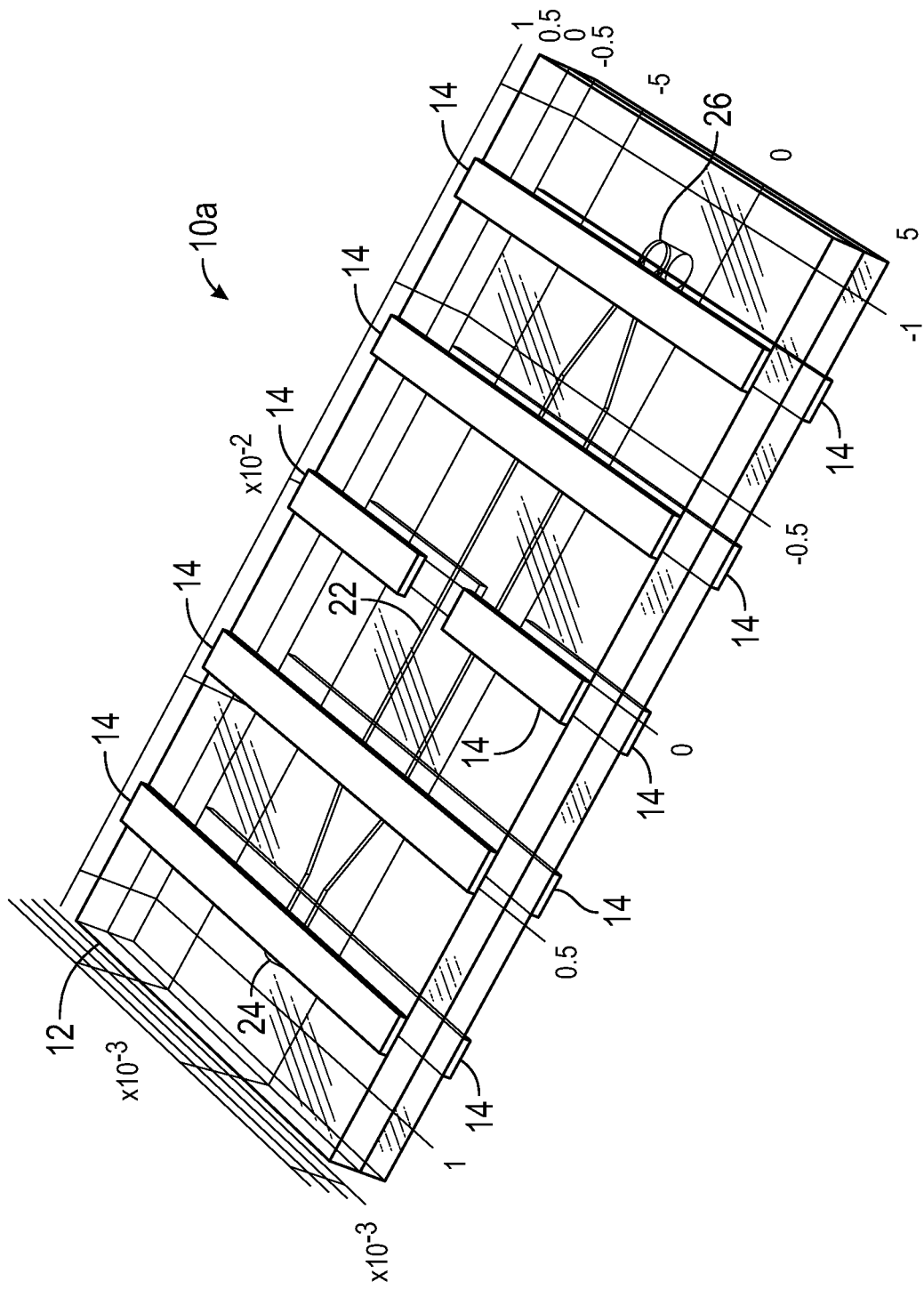
FIG. 21 is a perspective view of another exemplary acoustophoretic lysis device in accordance with the present disclosure.
Figure 22:
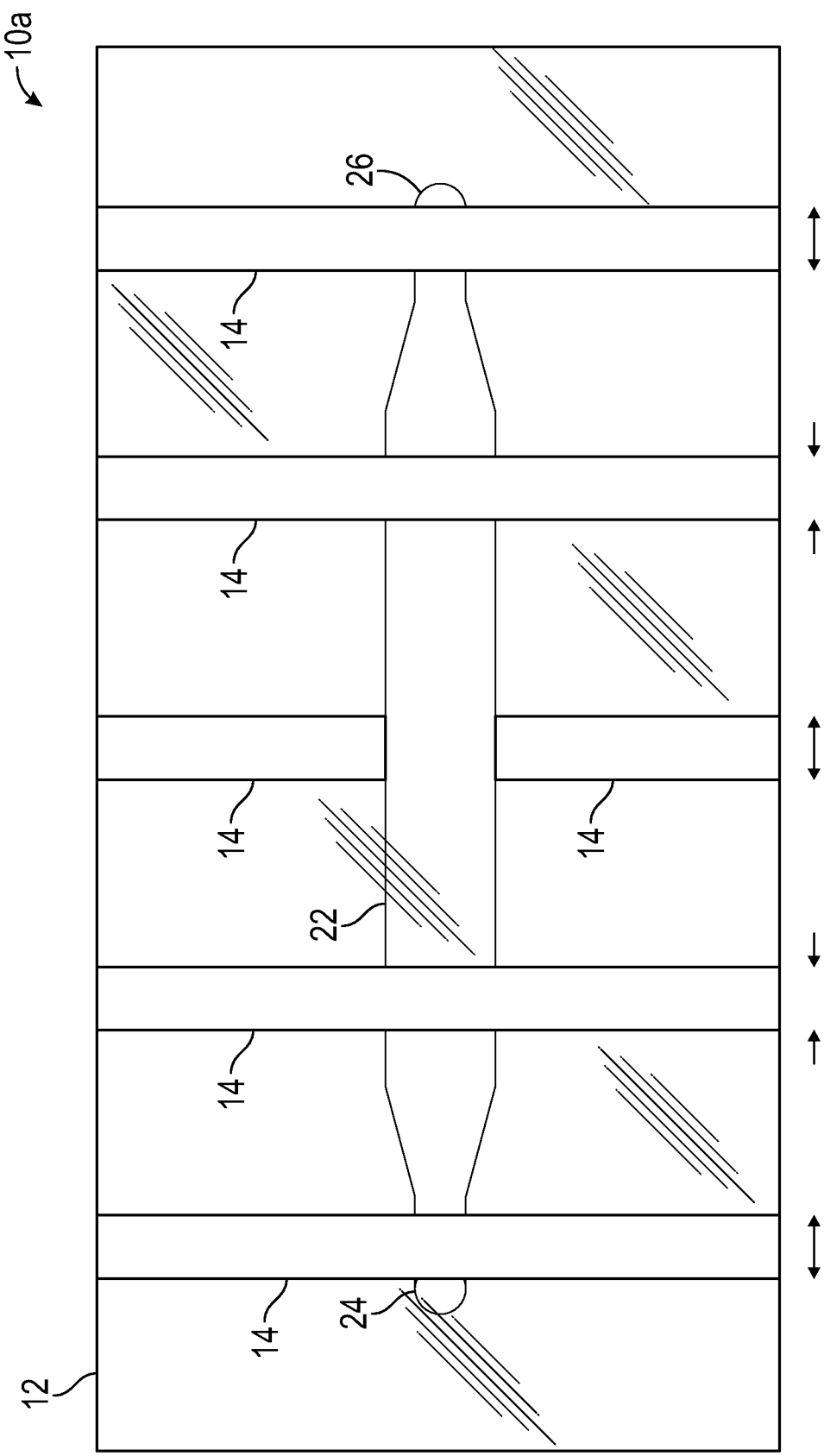
FIG. 22 is a plan view of the lysis device of FIG. 21.

FIGS. 21 and 22 illustrate another embodiment of an acoustophoretic lysis device 10a constructed in accordance with the inventive concepts disclosed herein. The lysis device 10a is similar in use and construction to the lysis device 10 except as described below. In some implementations, the lysis device 10a may include two or more acoustic transducers 14 bonded to the sample vessel 12 and perform as previously described.

Referring now to FIGS. 15-18, in some embodiments, the lysis device 10, 10a may be a component of an analyzer 100. The analyzer 100 may comprise the lysis device 10, 10a, an absorbance spectrophotometer 102, a fluidic distribution system 104 (for example, including a peristatic pump), and/or a controller 106. In one embodiment, the lysis device 10, 10a is removeable and/or exchangeable from the other components of the analyzer 100. In one embodiment, the analyzer 100 may further comprise a mount 108 configured to receive and/or position the lysis device 10. In one embodiment, the lysis device 10, 10a may be held (such as clamped) within the mount 108 such that the lysis device 10, 10a is able to vibrate and/or move within a range of vibration and/or movement.

In one embodiment, the analyzer 100 may further comprise one or more processors 140 and one or more non-transitory computer readable medium 142. In one embodiment, the one or more processors 140 and the one or more non-transitory computer readable medium 142 may be part of the controller 106. However, it will be understood that one or more of the processors 140 and/or the non-transitory computer readable medium 142 may be located external to the controller 106 and/or external to the other components of the analyzer 100. In one implementation, the analyzer 100 may comprise and/or be connectable to one or more sensor cartridge 143 having blood gas sensors 144, and/or one or more reagents cartridge 145.

In one embodiment, the absorbance spectrophotometer 102 may comprise a transmitter 112 and a receiver 114 positioned adjacent to the sample vessel 12, the transmitter 112 positioned to emit a medium 116 through the top 40, the bottom 42, and the microchannel 22, and the receiver 114 is positioned to receive at least a portion of the medium 116 after the portion of the medium 116 has passed through the top 40, the bottom 42, and the microchannel 22. In one embodiment, the transmitter 112 may be a light source and the medium 116 may be light. The light source may be one or more light emitting diode, for example. In one embodiment, the light may be white light having wavelengths in a range from approximately 450-700 nanometers.

The absorbance spectrophotometer 102 may be configured to measure the intensity of light in a part of the spectrum, especially as transmitted or emitted by particular substances in the fluidic sample 52 in the microchannel 22 of the sample vessel 12. The absorbance spectrophotometer 102 may be configured to measure how much a chemical substance absorbs light by measuring the intensity of light as a beam of light passes through the blood sample 52, or other fluidic sample 52. Each compound in the sample or solution absorbs or transmits light over a particular range of wavelengths.

The fluidic distribution system 104 (see FIG. 17) may have an inlet 120 (see FIG. 16) fluidly connectable to the first port 24, and an outlet 122 (see FIG. 16) fluidly connectable to the second port 26 of the sample vessel 12 of the lysis device 10, 10a. The fluidic distribution system 104 may move one or more fluidic sample 52, such as a blank sample or a blood sample or a washing solution, through the inlet 120 through the first port 24 into the microchannel 22 of the sample vessel 12. In one embodiment, the fluidic distribution system 104 may flush the microchannel 22, expelling material within the microchannel 22 through the second port 26 of the sample vessel 12 and out of the outlet 122. The fluidic distribution system 104 may be operated automatically, manually, or a combination of automatically and manually.

The controller 106 may be electrically connected to the acoustic transducer 14 of the lysis device 10. The controller 106 may be configured to provide electrical signals to the acoustic transducer 14, that when received by the acoustic transducer 14 cause the acoustic transducer 14 to emit ultrasonic acoustic waves at one or more frequency and/or range of frequencies, including at the resonant frequency of the monolithic structure of the lysis device 10 plus the fluidic sample 52.

Figure 16:
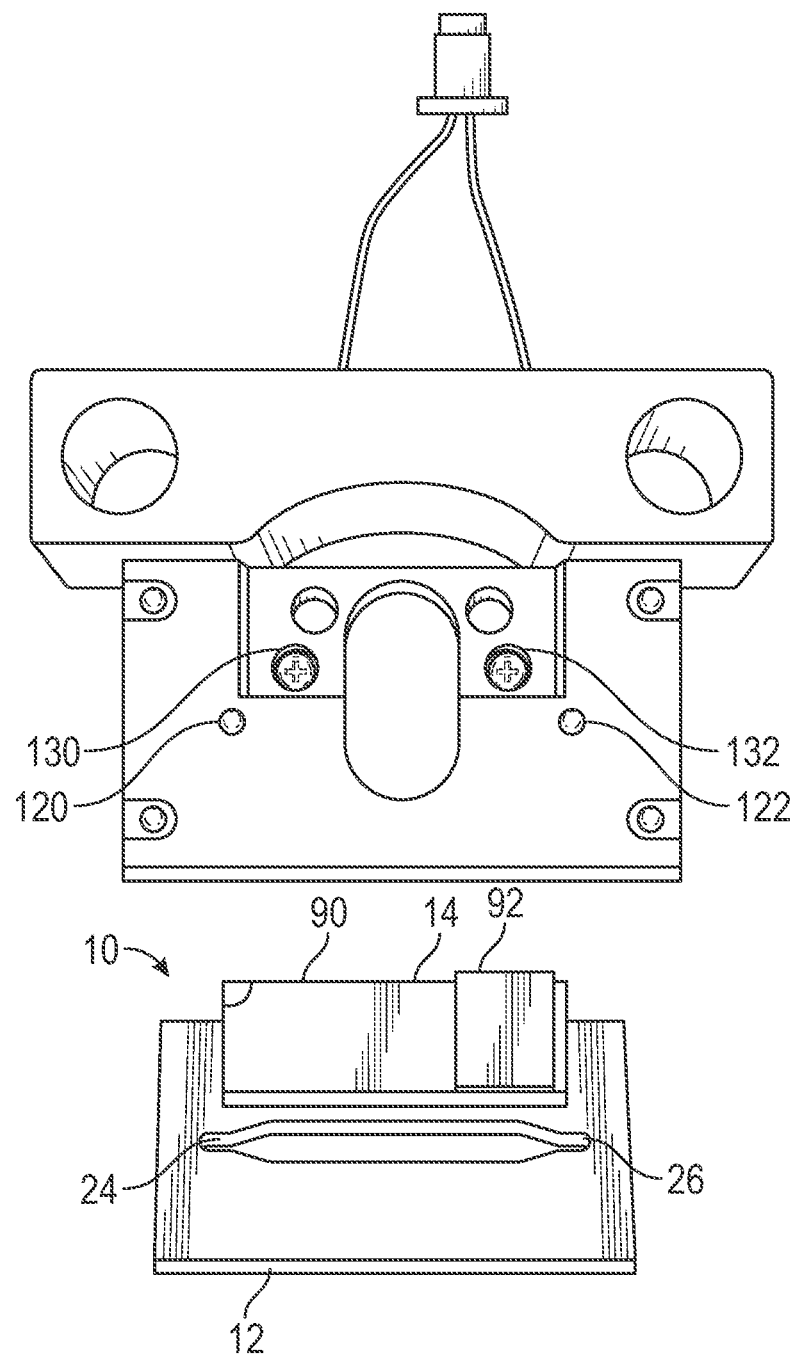
FIG. 16 is a perspective view of components of an exemplary analyzer in accordance with the present disclosure.

As shown in FIG. 16, in one embodiment the controller 106 may have a first electrical contact 130 and a second electrical contact 132. The first electric contact 130 and the second electric contact 132 may be electrically connectable to the first electrode 90 and the second electrode 92, respectively, of the acoustic transducer 14 of the lysis device 10 such that electrical potential may be provided to the acoustic transducer 14.

Figure 17:
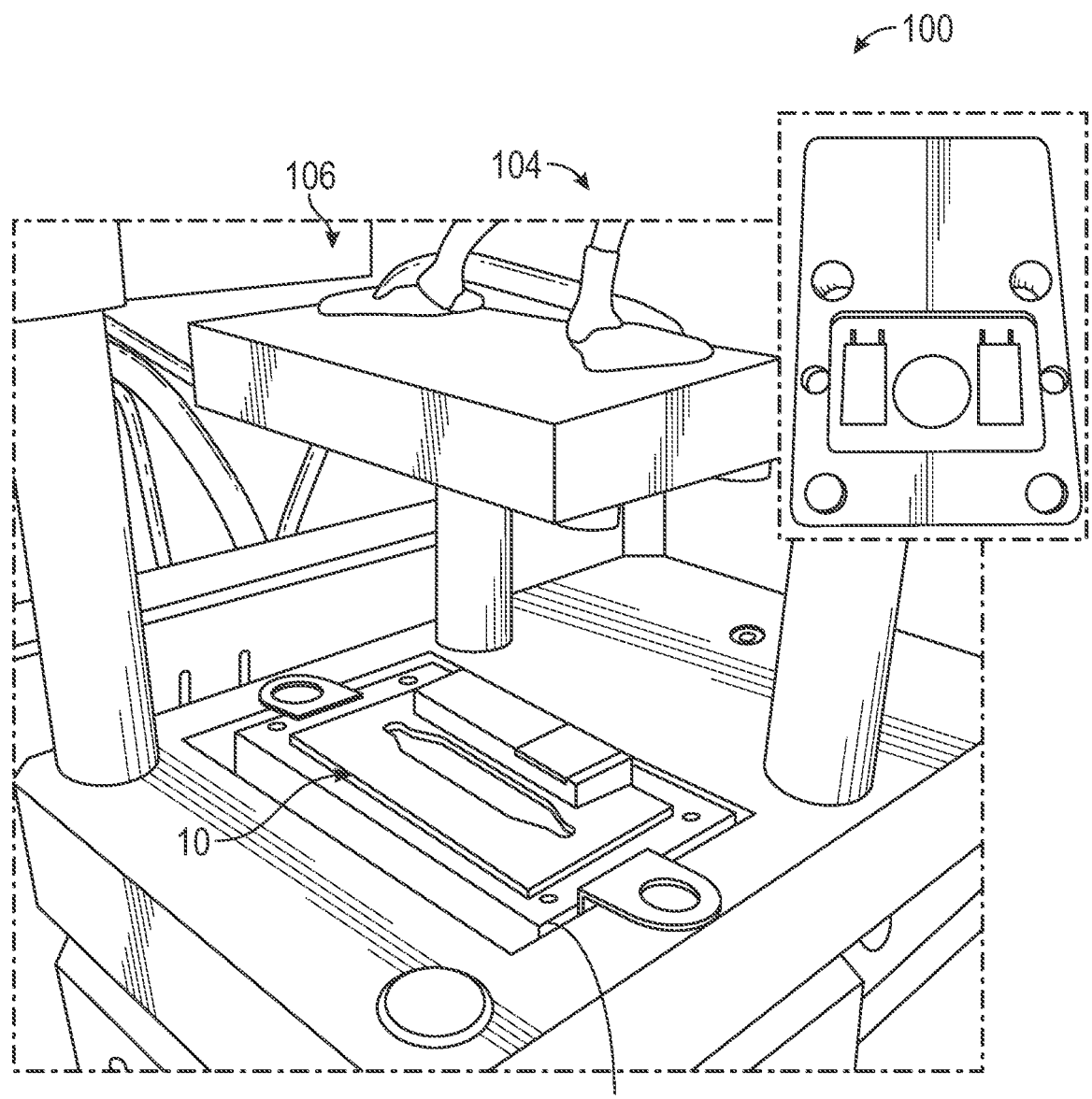
FIG. 17 is a perspective view of components of an exemplary analyzer in accordance with the present disclosure.
Figure 18:
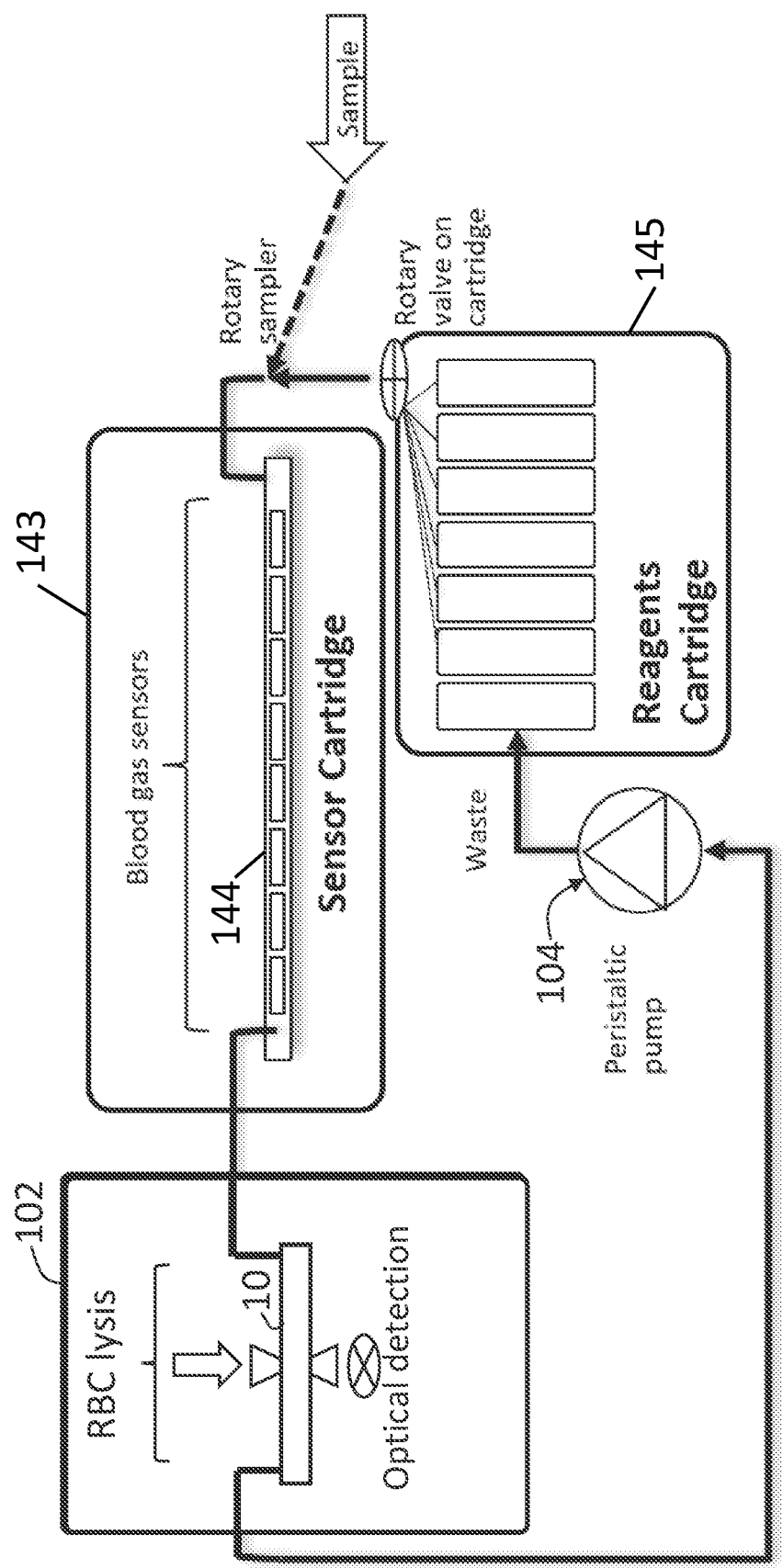
FIG. 18 is a schematic view of components of an exemplary analyzer in accordance with the present disclosure.

The mount 108 may hold the lysis device 10, 10a in place between the transmitter 112 and the receiver 114 and may position the lysis device 10, 10a to be operably connected to the fluidic distribution system 104 and the controller 106 (see FIG. 17). The mount 108 may be configured to stabilize the lysis device 10 in position without applying a force that would significantly change the acoustic impedance of the monolithic structure of the lysis device 10. For example, the mount 108 may include one or more clamps that apply a clamping force at or below approximately twenty newtons (N).

In one embodiment, the analyzer 100 may further comprise one or more digital temperature sensors and/or one or more thermal control element (such as Peltier elements).

In one embodiment, a method 200 for analyzing blood may comprise obtaining or receiving a blood sample 52; inputting the lysis device 10, 10a between the transmitter 112 and the receiver 114 of the absorbance spectrophotometer 102; inputting, with the fluidic distribution system 104, the blood sample 52 into the microchannel 22 of the sample vessel 12 via the inlet 120 and first port 24; activating the controller 106 to provide electrical signals to the acoustic transducer 14, that when received by the acoustic transducer 14 cause the acoustic transducer 14 to emit ultrasonic acoustic waves at one or more frequency and/or range of frequencies, including at the resonant frequency of the monolithic structure of the lysis device 10 plus the blood sample 52, and/or cause the acoustic transducer 14 to elongate and contract thereby producing shear forces in the blood sample 52 in the microchannel 22; such that cavitation is induced in the blood sample 52 causing the walls of the red blood cells of the blood sample 52 to rupture; activating the absorbance spectrophotometer 102 to transmit the medium 116 from the transmitter 112 through the lysed blood sample 52 to the receiver 114.

The method 200 may further comprise reading electrical signals generated by the receiver 114 to determine one or more oximetry parameters of the lysed blood sample 52 based at least in part on a signal indicative of the light received by the receiver 114 of the absorbance spectrophotometer 102.

Figure 19:
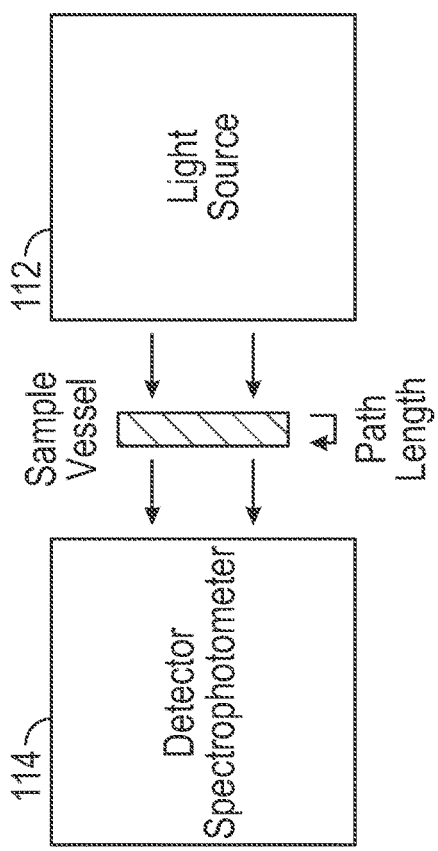
FIG. 19 is a schematic of determination of an absorption spectrum in accordance with the present disclosure.
Figure 20:
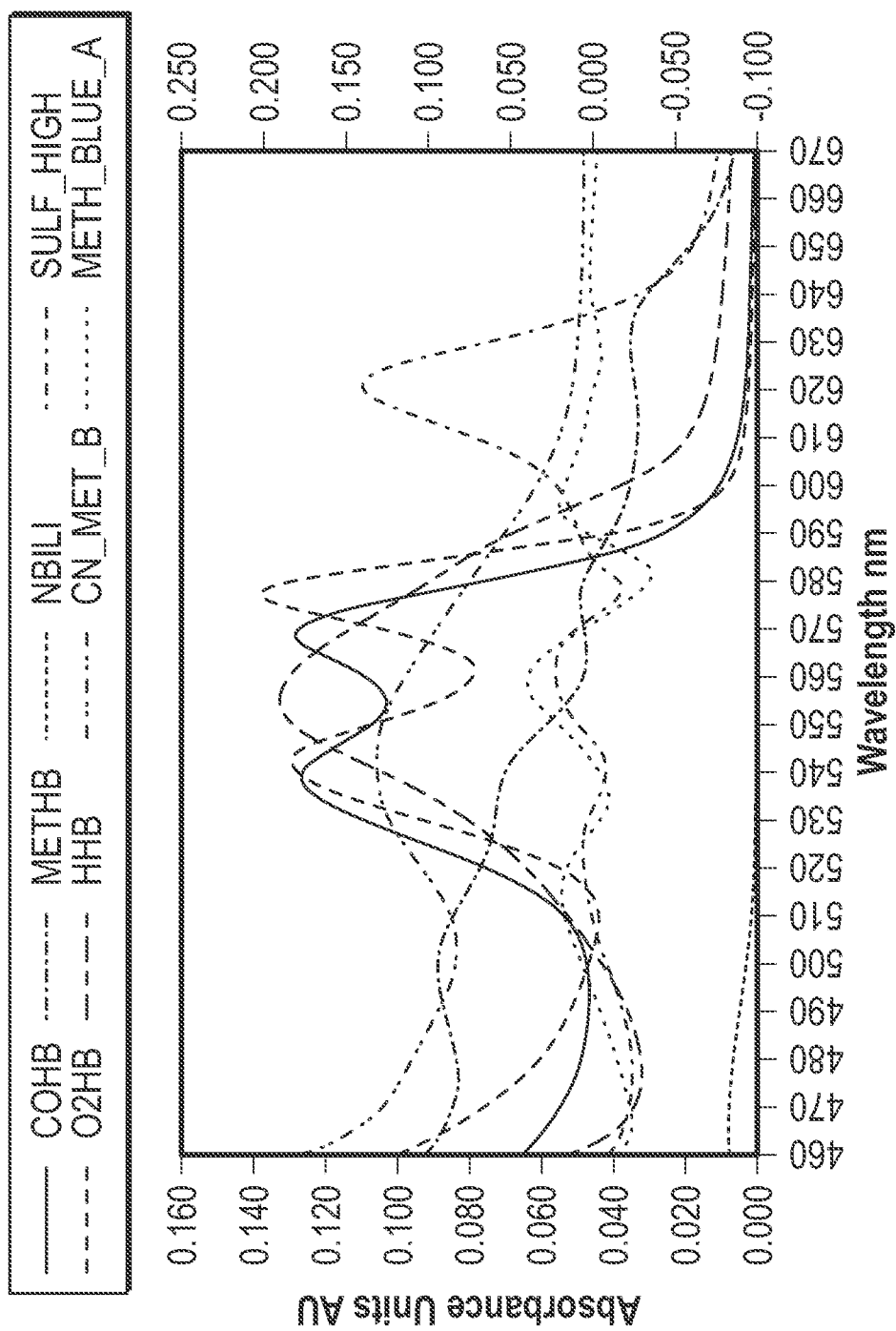
FIG. 20 illustrates spectral profile coefficients of the hemoglobin forms.

As shown in FIG. 19, an absorption spectrum may be calculated based on known calculations for absorption for liquid mediums. Further, as shown in FIG. 20, determining one or more oximetry parameters may further comprise analyzing spectral profile coefficients of hemoglobin forms, such as one or more of the following: carboxyhemoglobin (COHB), oxyhemoglobin (O2HB), methemoglobin (METHB), deoxyhemoglobin (HHB), neonatal Bilirubin (NBILI), Cyan Methemoglobin (CN_MET_B), Sulfhemoglobin (SULF_HIGH), and Methylene blue dye (METH_BLUE_A).

Determining one or more one or more oximetry parameters may be based on measurement of spectrophotometric optical absorption, that is the absorption of light by components in the blood sample 52.

Determining one or more one or more oximetry parameters may comprise measuring at least total hemoglobin (THB) and one or more of hemoglobin fractions, such as the following: oxyhemoglobin (O2HB), methemoglobin (METHB), deoxyhemoglobin (HHB), carboxyhemoglobin (COHB).

In one embodiment, the method 200 may comprise inputting and evacuating a wash solution into the microchannel 22 of the sample vessel 12 before and/or after introducing the blood sample 52 into the microchannel 22. The method 200 may further comprise activating the acoustic transducer 14 to produce acoustic waves and/or shear forces to agitate the wash solution in the microchannel 22. In one embodiment, the sample vessel 12 may be used, cleaned, and re-used. In one embodiment, the lysis device 10, 10a may not be reusable, and may be replaced for each new blood sample 52. In this embodiment, the lysis device 10 may be discarded after a single use.

The method 200 may further comprise calibrating the analyzer with a blank sample. In one embodiment, the fluidic sample 52 may be a test sample known as a "blank sample" that may be used to calibrate the analyzer 100. The blank sample may contain a die solution, which may be used to measure scattering of the transmission of the medium.

In one embodiment, the blood sample 52 may be approximately twelve microliters in volume. The blood sample typically comprises plasma and red blood cells (which may comprise 45%-60% of the blood sample) and possibly lipids.

In one embodiment, the blood sample 52 is held at a consistent temperature. In one embodiment, the temperature of the blood sample 52 is thirty-seven degrees Celsius plus or minus approximately 0.3 degree. In one embodiment, the temperature of the blood sample 52 is less than forty degrees Celsius, to avoid damage to the blood sample 52. In one embodiment, the blood sample 52 is held at a substantially consistent temperature utilizing the one or more temperature sensor and/or the one or more thermal control element.

An example of the analyzer 100 and the lysis device 10, 10a in use will now be described. In one example, the sample vessel 12 may be made of glass and may have a length-to-width aspect ratio in a range of about 1.4 to about 1.9, and the microchannel 22 may have a height-to-width aspect ratio of about 0.05 (for example, having a height of about 100 micrometers and a width of about two millimeters). The sample vessel 12 may be inserted in a path that the medium will travel between the transmitter 112 and the receiver 114 of the absorbance spectrophotometer 102. It should be understood that the analyzer 100 may be provided with various instruments including mirrors and/or waveguides to direct the medium through the path. The fluidic distribution system 104 may insert the blood sample 52 into the microchannel 22 of the sample vessel 12.

The controller 106 may be electrically connected to the acoustic transducer(s) 14 of the sample vessel 12, and may provide electrical signals to the acoustic transducer(s) 14 to cause the acoustic transducer 14 to emit ultrasonic sound waves through a range of frequencies from approximately 330 kHz to approximately 350 kHz in steps of approximately one kHz. The range of frequencies may be transmitted within a time period of approximately two seconds.

In one embodiment, the non-transitory computer readable medium 142 may store computer executable instructions that when executed by one or more processors 140 of the controller 106 may cause the one or more processors 140 to pass signals to the acoustic transducer(s) 14 connected to the sample vessel 12 having a microchannel 22 containing a whole blood sample 52 having blood cells and plasma, that cause the acoustic transducer 14(s) to emit ultrasonic acoustic waves into the sample vessel 12 at a frequency, intensity and duration to lyse the blood cells within the whole blood sample 52.

The frequency range includes the resonant frequency for the monolithic structure of the lysis device 10 with the blood sample 52, thereby causing cavitation in the blood sample 52, which ruptures the cell walls of the blood cells in the blood sample 52. Additionally, or alternatively, the controller 106 may cause the one or more processors 140 to pass signals to the acoustic transducer(s) 14 that cause the acoustic transducer(s) 14 to elongate and contract, thereby producing shear forces in the blood sample 52 in the microchannel 22, which rupture the cell walls of the blood cells in the blood sample 52.

A majority (more than 50%) of the cell walls of the blood cells may be ruptured.

The transmitter 112 of the absorbance spectrophotometer 102 may be activated to transmit the medium 116, such as light, through the sample vessel 12 into the lysed blood sample 52. The receiver 114 may receive at least portions of the medium 116 that exits the lysed blood sample 52 and the sample vessel 12. The receiver 114 may include one or more photodiodes, for example, for generating an electrical signal due to reception of the medium 116.

The analyzer 100, or the one or more computer processors 140, may determine one or more analytes present in the lysed blood sample 52 based at least in part on a signal indicative of the light received by the receiver 114 of the absorbance spectrophotometer 102. The analyzer 100, or one or more computer processors, may further analyze spectral profile coefficients of hemoglobin forms, such as one or more of the following: carboxyhemoglobin (COHB), oxyhemoglobin (O2HB), methemoglobin (METHB), deoxyhemoglobin (HHB), neonatal Bilirubin (NBILI), Cyan Methemoglobin (CN_MET_B), Sulfhemoglobin (SULF_HIGH), Methylene blue dye (METH_BLUE_A).

The analyzer 100, or the one or more computer processors 140, may measure total hemoglobin (THB) and/or one or more of hemoglobin fractions, such as the following: oxyhemoglobin (O2HB), methemoglobin (METHB), deoxyhemoglobin (HHB), carboxyhemoglobin (COHB).

The analyzer 100, or the one or more computer processors 140, may output the result of the analyses. The output may be shown on one or more display. The output may be used to determine treatment of the patient.

The following is a number list of non-limiting illustrative embodiments of the inventive concept disclosed herein:
 1. A lysis device, comprising:
 a sample vessel having an outer surface, a microchannel within the confines of the outer surface, a first port extending through the outer surface to the microchannel, and a second port extending through the outer surface to the microchannel, such that a blood sample is insertable through the first port into the microchannel; wherein the microchannel has a length, a width and a height, and wherein a microchannel aspect ratio of the width to the height is in a range from approximately 0.04 to approximately 0.175; and wherein the sample vessel has a width and a height, and wherein a sample vessel aspect ratio of the width to the height is in a range from approximately 0.5 to approximately 3.0; and
 an acoustic transducer bonded to the outer surface of the sample vessel to form a monolithic structure, the acoustic transducer configured to generate ultrasonic acoustic standing waves inside the blood sample in the microchannel and configured to bend the sample vessel such that shear forces are induced within the microchannel, the acoustic standing waves and the shear forces causing cavitation in the blood sample thereby rupturing cell walls in the blood sample.

2. The lysis device of illustrative embodiment 1, wherein the sample vessel is constructed of glass.

3. The lysis device of illustrative embodiment 1, wherein the sample vessel is constructed of a non-glass material having a Young's modulus within a range from about 50 Gpa to 90 Gpa.

4. The lysis device of illustrative embodiment 1, wherein the outer surface is a first outer surface having a mounting area, the mounting area having a first shape, and wherein the acoustic transducer has a second outer surface having a second shape corresponding to the first shape, the second outer surface of the acoustic transducer bonded to the mounting area.

5. The lysis device of illustrative embodiment 1, wherein the acoustic transducer matingly engages the outer surface of the sample vessel.

6. The lysis device of illustrative embodiment 1, wherein the height of the microchannel is about 100 micrometers.

7. The lysis device of illustrative embodiment 1, wherein the width of the microchannel is about two millimeters.

8. The lysis device of illustrative embodiment 1, wherein the microchannel aspect ratio of the width to the height of the microchannel is about 0.05.

9. An analyzer, comprising:
a lysis device, comprising:
  a sample vessel having an outer surface, a microchannel within the confines of the outer surface, a first port extending through the outer surface to the microchannel, and a second port extending through the outer surface to the microchannel, such that a blood sample is insertable through the first port into the microchannel; wherein the microchannel has a length, a width and a height, and wherein a microchannel aspect ratio of the width to the height is in a range from approximately 0.04 to approximately 0.175; and wherein the sample vessel has a width and a height, and wherein a sample vessel aspect ratio of the width to the height is in a range from approximately 0.5 to approximately 3.0; and
  an acoustic transducer bonded to the outer surface of the sample vessel to form a monolithic structure, the acoustic transducer configured to generate ultrasonic acoustic standing waves inside the blood sample in the microchannel and configured to bend the sample vessel such that shear forces are induced within the microchannel, the acoustic standing waves and the shear forces causing cavitation in the blood sample thereby rupturing cell walls in the blood sample;
an absorbance spectrophotometer comprising a transmitter and a receiver positioned adjacent to the sample vessel, the transmitter positioned to emit a light medium through the microchannel, and a receiver positioned to receive at least a portion of the light medium after the portion of the light medium has passed through the microchannel;
a fluidic distribution system having an outlet connected to the first port, and an inlet connected to the second port; and
a controller electrically connected to the acoustic transducer and configured to provide electrical signals to the acoustic transducer that when received by the acoustic transducer cause the acoustic transducer to emit ultrasonic acoustic waves and cause the acoustic transducer to contract and elongate.

10. The analyzer of illustrative embodiment 9, wherein the outer surface of the sample vessel has a first side, and a second side opposite the first side, the transmitter being positioned on the first side of the sample vessel, and the receiver being positioned on the second side of the sample vessel, the sample vessel being constructed of a material transparent to the light medium.

11. The analyzer of illustrative embodiment 9, wherein the outer surface of the sample vessel has a first side, and a second side opposite the first side, the first side and the second side being planar.

12. The analyzer of illustrative embodiment 9, wherein the sample vessel is constructed of glass.

13. The analyzer of illustrative embodiment 9, wherein the sample vessel is constructed of a non-glass material having a Young's modulus within a range from about 50 Gpa to 90 Gpa.

14. The analyzer of illustrative embodiment 9, wherein the outer surface of the sample vessel is a first outer surface having a mounting area, the mounting area having a first shape, and wherein the acoustic transducer has a second outer surface having a second shape corresponding to the first shape, the second outer surface of the acoustic transducer bonded to the mounting area.

15. The analyzer of illustrative embodiment 9, wherein the acoustic transducer matingly engages the outer surface of the sample vessel.

16. The analyzer of illustrative embodiment 9, wherein the height of the microchannel is about 100 micrometers and the width of the microchannel is about two millimeters.

17. A method of making a lysis device, comprising:
bonding an acoustic transducer to an outer surface of a sample vessel to form a monolithic structure, the sample vessel having a microchannel within the confines of the outer surface, a first port extending through the outer surface to the microchannel, a second port extending through the outer surface to the microchannel, the microchannel having a length, a width and a height, and a microchannel aspect ratio of the width to the height in a range from approximately 0.04 to approximately 0.175; and wherein the sample vessel has a width and a height, and wherein a sample vessel aspect ratio of the width to the height is in a range from approximately 0.5 to approximately 3.0; the acoustic transducer having a first resonant frequency, the monolithic structure having a second resonant frequency spaced spectrally from the first resonant frequency, the acoustic transducer configured to emit ultrasonic acoustic waves at the second resonant frequency of the monolithic structure.

18. A lysis method, comprising:
passing a whole blood sample into a microchannel of a sample vessel, the sample vessel being bonded to an acoustic transducer such that the sample vessel and the acoustic transducer are a monolithic structure, the acoustic transducer having a first resonant frequency, the monolithic structure having a second resonant frequency spectrally spaced from the first resonant frequency, the whole blood sample having blood cells and plasma; the sample vessel having an outer surface, a first port extending through the outer surface to the microchannel, and a second port extending through the outer surface to the microchannel, such that the whole blood sample is insertable through the first port into the microchannel; wherein the microchannel has a length, a width and a height, and wherein a microchannel aspect ratio of the width to the height is in a range from approximately 0.04 to approximately 0.175; and wherein the sample vessel has a width and a height, and wherein a sample vessel aspect ratio of the width to the height is in a range from approximately 0.5 to approximately 3.0; and providing electrical signals to the acoustic transducer to cause the acoustic transducer to emit ultrasonic acoustic waves at the second resonant frequency with an intensity and duration to lyse the blood cells within the whole blood sample within the microchannel of the sample vessel.

19. The method of illustrative embodiment 18, wherein providing electrical signals includes providing electrical signals to the acoustic transducer to cause the acoustic transducer to emit ultrasonic acoustic waves at a plurality of frequencies in a range encompassing the second resonant frequency.

20. The method of illustrative embodiment 19, wherein the range is from about 320 kHz to about 350 kHz.

21. A non-transitory computer readable medium storing computer executable instructions that when executed by one or more processors of a controller cause the one or more processors to pass signals to a single acoustic transducer connected to a sample vessel having a microchannel containing a whole blood sample having blood cells and plasma, that cause the single acoustic transducer to emit ultrasonic acoustic waves into the sample vessel at a frequency, intensity and duration to lyse the blood cells within the whole blood sample; the sample vessel having an outer surface, a first port extending through the outer surface to the microchannel, and a second port extending through the outer surface to the microchannel, such that the whole blood sample is insertable through the first port into the microchannel; wherein the microchannel has a length, a width and a height, and wherein a microchannel aspect ratio of the width to the height is in a range from approximately 0.04 to approximately 0.175; and wherein the sample vessel has a width and a height, and wherein a sample vessel aspect ratio of the width to the height is in a range from approximately 0.5 to approximately 3.0.

22. A lysis device, comprising:
a sample vessel having an outer surface, a microchannel within the confines of the outer surface, a first port extending through the outer surface to the microchannel, and a second port extending through the outer surface to the microchannel, such that a blood sample is insertable through the first port into the microchannel; and
an acoustic transducer bonded to the outer surface of the sample vessel to form a monolithic structure, the acoustic transducer configured to generate ultrasonic acoustic standing waves inside the blood sample in the microchannel and configured to bend the sample vessel such that shear forces are induced within the microchannel, the acoustic standing waves and the shear forces being of sufficient magnitude to cause cavitation in the blood sample and thereby rupture cell walls in the blood sample.

CONCLUSION

Conventionally, blood analysis was not available at the point-of-care of patients or was time consuming and expensive. In accordance with the present disclosure, the lysis device 10 is disclosed which provides improved accuracy and precision of measured parameters of a blood sample within a desired time-to-result at the point of care of a patient, and that is more easily manufactured and with less cost, wherein the lysis device 10 is configured to cooperate with the analyzer 100. The lysis device 10, 10a may be configured to lyse red blood cells in a sample vessel by means of ultrasonic acoustic waves, pressure, fluid movement, and/or shear forces, generated in the vessel by a single acoustic transducer driven at one or more particular excitation frequency, or range of frequencies The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Even though particular combinations of features and steps are recited in the claims and/or disclosed in the specification, these combinations are not intended to limit the disclosure. In fact, many of these features and steps may be combined in ways not specifically recited in the claims and/or disclosed in the specification. Although each dependent claim listed below may directly depend on only one other claim, the disclosure includes each dependent claim in combination with every other claim in the claim set.

No element, act, or instruction used in the present application should be construed as critical or essential to the invention unless explicitly described as such outside of the preferred embodiment. Further, the phrase "based on" is intended to mean "based, at least in part, on" unless explicitly stated otherwise.

What is claimed is:

1. A lysis device, comprising:
a sample vessel having an outer surface, a microchannel within confines of the outer surface, a first port extending through the outer surface to the microchannel, and a second port extending through the outer surface to the microchannel, such that a blood sample is insertable through the first port into the microchannel; wherein the microchannel has a length, a width and a height, and wherein a microchannel aspect ratio of the width to the height is in a range from approximately 0.04 to approximately 0,175; and wherein the sample vessel has a width and a height, and wherein a sample vessel aspect ratio of the width to the height is in a range from approximately 0.5 to approximately 3.0; and
an acoustic transducer bonded to the outer surface of the sample vessel to form a monolithic structure, the acoustic transducer configured to generate ultrasonic acoustic standing waves inside the blood sample in the microchannel and configured to bend the sample vessel such that shear forces are induced within the microchannel, the acoustic standing waves and the shear forces configured to induce cavitation in the blood sample, such that the acoustic standing waves are configured to rupture cell walls of a cell in the blood sample, and configured to release hemoglobin from within the cell.

2. The lysis device of claim 1, wherein the sample vessel is constructed of glass.

3. The lysis device of claim 1, wherein the sample vessel is constructed of a non-glass material having a Young's modulus within a range from about 50 Gpa to 90 Gpa.

4. The lysis device of claim 1, wherein the outer surface is a first outer surface having a mounting area, the mounting area having a first shape, and wherein the acoustic transducer has a second outer surface having a second shape corresponding to the first shape, the second outer surface of the acoustic transducer bonded to the mounting area.

5. The lysis device of claim 1, wherein the acoustic transducer matingly engages the outer surface of the sample vessel.

6. The lysis device of claim 1, wherein the height of the microchannel is about 100 micrometers.

7. The lysis device of claim 1, wherein the width of the microchannel is about two millimeters.

8. The lysis device of claim 1, wherein the microchannel aspect ratio of the width to the height of the microchannel is about 0.05.

9. An analyzer, comprising:
a lysis device, comprising:
a sample vessel having an outer surface, a microchannel within confines of the outer surface, a first port extending through the outer surface to the microchannel, and a second port extending through the outer surface to the microchannel, such that a blood sample is insertable through the first port into the microchannel; wherein the microchannel has a length, a width and a height, and wherein a microchannel aspect ratio of the width to the height is in a range from approximately 0.04 to approximately 0.175; and wherein the sample vessel has a width and a height, and wherein a sample vessel aspect ratio of the width to the height is in a range from approximately 0.5 to approximately 3.0; and
an acoustic transducer bonded to the outer surface of the sample vessel to form a monolithic structure, the acoustic transducer configured to generate ultrasonic acoustic standing waves inside the blood sample in the microchannel and configured to bend the sample vessel such that shear forces are induced within the microchannel, the acoustic standing waves and the shear forces configured to induce cavitation in the blood sample, such that the acoustic standing waves are configured to rupture cell walls of a cell in the blood sample, and configured to release hemoglobin from within the cell; an absorbance spectrophotometer comprising a transmitter and a receiver positioned adjacent to the sample vessel, the transmitter positioned to emit a light medium through the microchannel, and a receiver positioned to receive at least a portion of the light medium after the portion of the light medium has passed through the microchannel;
a fluidic distribution system having an outlet connected to the first port, and an inlet connected to the second port; and
a controller electrically connected to the acoustic transducer and configured to provide electrical signals to the acoustic transducer that when received by the acoustic transducer cause the acoustic transducer to emit ultrasonic acoustic waves and cause the acoustic transducer to contract and elongate.

10. The analyzer of claim 9, wherein the outer surface of the sample vessel has a first side, and a second side opposite the first side; the transmitter being positioned on the first side of the sample vessel, and the receiver being positioned on the second side of the sample vessel; the sample vessel being constructed of a material transparent to the light medium.

11. The analyzer of claim 9, wherein the outer surface of the sample vessel has a first side; and a second side opposite the first side, the first side and the second side being planar.

12. The analyzer of claim 9, wherein the sample vessel is constructed of glass.

13. The analyzer of claim 9, wherein the sample vessel is constructed of a non-glass material having a Young's modulus within a range from about 50 Gpa to 90 Gpa.

14. The analyzer of claim 9, wherein the outer surface of the sample vessel is a first outer surface having a mounting area, the mounting area having a first shape, and wherein the acoustic transducer has a second outer surface having a second shape corresponding to the first shape, the second outer surface of the acoustic transducer bonded to the mounting area.

15. The analyzer of claim 9, wherein the acoustic transducer matingly engages the outer surface of the sample vessel.

16. The analyzer of claim 9, wherein the height of the microchannel is about 100 micrometers and the width of the microchannel is about two millimeters.

17. A method of making a lysis device; comprising:
bonding an acoustic transducer to an outer surface of a sample vessel to form a monolithic structure, the sample vessel having a microchannel within confines of the outer surface, a first port extending through the outer surface to the microchannel, a second port extending through the outer surface to the microchannel, the microchannel having a length, a width and a height, and a microchannel aspect ratio of the width to the height in a range from approximately 0.04 to approximately 0.175; and wherein the sample vessel has a width and a height, and wherein a sample vessel aspect ratio of the width to the height is in a range from approximately 0.5 to approximately 3.0; the acoustic transducer having a first resonant frequency, the monolithic structure having a second resonant frequency spaced spectrally from the first resonant frequency, the acoustic transducer configured to emit ultrasonic acoustic waves at the second resonant frequency of the monolithic structure and the acoustic transducer configured to rupture cell walls of a cell in the blood sample, and configured to release hemoglobin from within the cell.

18. A lysis method, comprising:
passing a whole blood sample into a microchannel of a sample vessel, the sample vessel being bonded to an acoustic transducer such that the sample vessel and the acoustic transducer are a monolithic structure, the acoustic transducer having a first resonant frequency; the monolithic structure having a second resonant frequency spectrally spaced from the first resonant frequency, the whole blood sample having blood cells and plasma; the sample vessel having an outer surface, a first port extending through the outer surface to the microchannel, and a second port extending through the outer surface to the microchannel, such that the whole blood sample is insertable through the first port into the microchannel; wherein the microchannel has a length, a width and a height, and wherein a microchannel aspect ratio of the width to the height is in a range from approximately 0.04 to approximately 0.175; and wherein the sample vessel has a width and a height, and wherein a sample vessel aspect ratio of the width to the height is in a range from approximately 0.5 to approximately 3.0; and
providing electrical signals to the acoustic transducer to cause the acoustic transducer to emit ultrasonic acoustic waves at the second resonant frequency with an intensity and duration, the ultrasonic acoustic waves rupturing cell walls of a blood cell in the whole blood sample, to release hemoglobin from within the blood cell within the microchannel of the sample vessel.

19. The method of claim 18, wherein providing electrical signals includes providing electrical signals to the acoustic transducer to cause the acoustic transducer to emit ultrasonic acoustic waves at a plurality of frequencies in a range encompassing the second resonant frequency.

20. The method of claim 19, wherein the range is from about 320 kHz to about 350 kHz.

21. A non-transitory computer readable medium storing computer executable instructions that when executed by one or more processors of a controller are programmed to cause the one or more processors to pass signals to a single acoustic transducer connected to a sample vessel having a microchannel containing a whole blood sample having blood cells and plasma, that cause the single acoustic transducer to emit ultrasonic acoustic waves into the sample vessel at a frequency, intensity and duration and wherein the acoustic transducer is configured to rupture cell walls of a blood cell in the whole blood sample, such that the ultrasonic waves are configured to release hemoglobin from within the blood cell; the sample vessel having an outer surface, a first port extending through the outer surface to the microchannel, and a second port extending through the outer surface to the microchannel, such that the whole blood sample is insertable through the first port into the microchannel; wherein the microchannel has a length, a width and a height; and wherein a microchannel aspect ratio of the width to the height is in a range from approximately 0.04 to approximately 0.175; and wherein the sample vessel has a width and a height, and wherein a sample vessel aspect ratio of the width to the height is in a range from approximately 0.5 to approximately 3.0.

22. A lysis device, comprising:
    a sample vessel having an outer surface, a microchannel within confines of the outer surface, a first port extending through the outer surface to the microchannel, and a second port extending through the outer surface to the microchannel, such that a blood sample is insertable through the first port into the microchannel; and
    an acoustic transducer bonded to the outer surface of the sample vessel to form a monolithic structure, the acoustic transducer configured to generate ultrasonic acoustic standing waves inside the blood sample in the microchannel and configured to bend the sample vessel such that shear forces are induced within the microchannel, the acoustic standing waves and the shear forces configured to induce cavitation in the blood sample, such that the acoustic standing waves are configured to rupture cell walls of a cell in the blood sample, and configured to release hemoglobin from with the cell.

* * * * *